US012654032B2

(12) United States Patent
Knox

(10) Patent No.: US 12,654,032 B2
(45) Date of Patent: Jun. 16, 2026

(54) CONTROLLING OPERATION OF A RADIOTHERAPY DEVICE

(71) Applicant: Elekta Limited, Crawley (GB)

(72) Inventor: Christopher Knox, Crawley (GB)

(73) Assignee: Elekta Limited, Crawley (GB)

( * ) Notice: Subject to any disclaimer, the term of this patent is extended or adjusted under 35 U.S.C. 154(b) by 351 days.

(21) Appl. No.: 18/246,721

(22) PCT Filed: Sep. 30, 2021

(86) PCT No.: PCT/EP2021/077044
§ 371 (c)(1),
(2) Date: Mar. 27, 2023

(87) PCT Pub. No.: WO2022/069688
PCT Pub. Date: Apr. 7, 2022

(65) Prior Publication Data
US 2023/0381538 A1 Nov. 30, 2023

(30) Foreign Application Priority Data
Sep. 30, 2020 (GB) ..................................... 2015544

(51) Int. Cl.
*A61N 5/10* (2006.01)

(52) U.S. Cl.
CPC ............. *A61N 5/1031* (2013.01); *A61N 5/10* (2013.01); *A61N 5/103* (2013.01); *A61N 5/1037* (2013.01);
(Continued)

(58) Field of Classification Search
CPC ........ A61N 5/10; A61N 5/103; A61N 5/1031; A61N 5/1037; A61N 5/1042;
(Continued)

(56) References Cited

U.S. PATENT DOCUMENTS 6,118,847 A * 9/2000 Hernandez-Guerra ...................... A61N 5/1048
378/65
6,144,875 A * 11/2000 Schweikard ........... A61B 90/10
378/69
(Continued)

FOREIGN PATENT DOCUMENTS

EP 0940158 A1 9/1999
WO WO-2009052847 A1 4/2009
(Continued)

OTHER PUBLICATIONS

"International Application Serial No. PCT/EP2021/077044, International Search Report dated Jan. 12, 2022", (Jan. 12, 2022), 7 pgs.
(Continued)

*Primary Examiner* — Allen C. Ho
(74) *Attorney, Agent, or Firm* — Schwegman Lundberg & Woessner, P.A.

(57) ABSTRACT

Disclosed herein is a computer-implemented method of determining a control scheme for operating a radiotherapy device for delivery of a radiation dose via a radiotherapy treatment beam to a target. The radiotherapy device comprises abeam generation apparatus that is configured to output radiation via a radiotherapy treatment beam, and wherein operation of the radiotherapy device can be described using at least one operational parameter. The method comprises determining the control scheme by identifying a first time (t1) at which at least a first portion of the radiation dose is to be delivered at a first radiation delivery rate; and identifying a second time (t2) for the radiotherapy device to undergo a cool-down period, wherein during the cool-down period the radiation delivery rate is less than the first radiation delivery rate; wherein the control scheme is
(Continued)

determined such that at least one criterion associated with the at least one operational parameter is met.

17 Claims, 5 Drawing Sheets

(52) U.S. Cl.
CPC ......... *A61N 5/1045* (2013.01); *A61N 5/1047* (2013.01); *A61N 5/1048* (2013.01); *A61N 5/1067* (2013.01); *A61N 5/1068* (2013.01); *A61N 5/1081* (2013.01); *A61N 2005/1072* (2013.01); *A61N 2005/1089* (2013.01)

(58) Field of Classification Search
CPC .. A61N 5/1045; A61N 5/1047; A61N 5/1048; A61N 5/1049; A61N 2005/1052; A61N 2005/1054; A61N 2005/1055; A61N 2005/1061; A61N 5/1064; A61N 5/1065; A61N 5/1067; A61N 5/1068; A61N 5/1069; A61N 5/107; A61N 5/1071; A61N 2005/1072; A61N 2005/1074; A61N 5/1077; A61N 5/1081; A61N 2005/1089
USPC .......................................................... 378/65
See application file for complete search history.

(56) References Cited

U.S. PATENT DOCUMENTS

| | | | | | |
|---|---|---|---|---|---|
| 6,385,286 | B1 * | 5/2002 | Fitchard | ............... | A61N 5/1042 378/65 |
| 6,385,288 | B1 * | 5/2002 | Kanematsu | .......... | A61N 5/1042 378/65 |
| 6,621,889 | B1 * | 9/2003 | Mostafavi | ........... | A61N 5/1048 378/65 |
| 6,690,965 | B1 * | 2/2004 | Riaziat | ................... | A61B 6/463 378/65 |
| 6,977,987 | B2 * | 12/2005 | Yamashita | ............... | A61N 5/10 378/65 |
| 7,171,257 | B2 * | 1/2007 | Thomson | ............. | A61N 5/1049 378/69 |
| 7,239,684 | B2 * | 7/2007 | Hara | .................... | A61N 5/1049 378/65 |
| 7,257,436 | B2 * | 8/2007 | Sasaki | .................... | A61B 6/541 600/407 |
| 7,469,035 | B2 * | 12/2008 | Keall | .................. | A61N 5/1042 378/65 |
| 7,505,559 | B2 * | 3/2009 | Kuduvalli | ........... | A61N 5/1049 378/65 |
| 7,551,717 | B2 * | 6/2009 | Tome | ................... | A61B 5/6831 378/65 |
| 7,570,738 | B2 * | 8/2009 | Khamene | ............... | A61B 6/032 378/65 |
| 7,609,810 | B2 * | 10/2009 | Yi | ........................ | A61N 5/1049 378/65 |
| 7,713,205 | B2 * | 5/2010 | Fu | ........................ | A61N 5/1049 600/443 |
| 7,835,493 | B2 * | 11/2010 | Keall | .................. | A61N 5/1042 378/65 |
| 7,894,649 | B2 * | 2/2011 | Fu | ........................ | A61N 5/1049 378/65 |
| 7,906,770 | B2 * | 3/2011 | Otto | ..................... | A61N 5/1047 378/65 |
| 7,935,939 | B2 * | 5/2011 | Aoi | ...................... | A61N 5/1049 250/493.1 |
| 7,961,843 | B2 * | 6/2011 | Brown | ................. | A61N 5/1047 378/65 |
| 8,027,715 | B2 * | 9/2011 | Sayeh | ................... | A61B 5/113 378/69 |
| 8,042,209 | B2 * | 10/2011 | D'Souza | ............. | A61N 5/1049 5/610 |
| 8,130,907 | B2 * | 3/2012 | Maurer, Jr. | ........... | A61B 6/542 378/65 |
| 8,238,519 | B2 * | 8/2012 | Bani-Hashemi | ..... | A61N 5/1049 378/65 |
| 8,280,002 | B2 * | 10/2012 | Bani-Hashemi | ..... | A61N 5/1064 378/65 |
| 8,559,596 | B2 * | 10/2013 | Thomson | ............. | A61B 6/4071 378/65 |
| 8,619,945 | B2 * | 12/2013 | Stahl | .................... | A61N 5/1045 378/65 |
| 10,279,196 | B2 * | 5/2019 | West | .................... | A61N 5/1031 |
| 10,688,320 | B2 * | 6/2020 | Voronenko | .......... | A61N 5/1045 |
| 10,888,712 | B2 * | 1/2021 | Fredriksson | ......... | A61N 5/1037 |
| 11,141,609 | B2 * | 10/2021 | Tilly | ................... | A61N 5/1042 |
| 11,679,276 | B2 * | 6/2023 | Novosad | ............. | A61N 5/1049 378/65 |
| 11,786,755 | B2 * | 10/2023 | Ohishi | ................. | A61N 5/1039 600/1 |
| 11,983,869 | B2 * | 5/2024 | Hébert | ................ | A61N 5/1037 |
| 12,042,673 | B2 * | 7/2024 | Ohishi | ................ | A61N 5/1081 |
| 12,097,387 | B2 * | 9/2024 | Ichihashi | ............. | A61N 5/1037 |
| 12,109,052 | B2 * | 10/2024 | Baba | .................... | A61N 5/1049 |
| 12,115,386 | B2 * | 10/2024 | Voronenko | .......... | A61N 5/1031 |
| 12,115,392 | B2 * | 10/2024 | Brown | ................. | A61N 5/1049 |
| 12,133,993 | B2 * | 11/2024 | Novosad | .............. | A61N 5/1049 |
| 12,201,852 | B2 * | 1/2025 | Smith | .................. | A61N 5/1037 |
| 12,239,852 | B2 * | 3/2025 | Thomas | ................ | A61N 5/103 |
| 12,251,577 | B2 * | 3/2025 | Riad | ..................... | A61N 5/107 |
| 12,257,453 | B2 * | 3/2025 | Knox | .................. | A61N 5/1039 |
| 12,274,895 | B2 * | 4/2025 | Tilly | .................. | A61N 5/1071 |
| 12,364,877 | B2 * | 7/2025 | Hirai | ................... | A61N 5/1049 |
| 12,377,288 | B2 * | 8/2025 | Duan | .................. | A61N 5/1031 |
| 12,496,034 | B2 * | 12/2025 | Maltz | .................. | A61N 5/1049 |
| 12,502,553 | B2 * | 12/2025 | Sayeed | ................ | A61N 5/1037 |
| 2008/0144772 | A1 | 6/2008 | Yi et al. | | |
| 2016/0030769 | A1 | 2/2016 | Cameron et al. | | |

FOREIGN PATENT DOCUMENTS

| | | |
|---|---|---|
| WO | WO-2010150175 A1 | 12/2010 |
| WO | WO-2019090314 A1 | 5/2019 |
| WO | WO-2020107121 A1 | 6/2020 |

OTHER PUBLICATIONS

"International Application Serial No. PCT/EP2021/077044, Written Opinion dated Jan. 12, 2022", (Jan. 12, 2022), 11 pgs.
"United Kingdom Application Serial No. 2015544.6, Examination Report dated Mar. 10, 2021", (Mar. 10, 2021), 6 pgs.

* cited by examiner

CONTROLLING OPERATION OF A RADIOTHERAPY DEVICE

PRIORITY APPLICATIONS

This application is a U.S. National Stage Filing under 35 U.S.C. § 371 from International Application No. PCT/EP2021/077044, filed on Sep. 30, 2021, and published as WO2022/069688 on Apr. 7, 2022, which claims the benefit of priority to British Application No. 2015544.6, filed on Sep. 30, 2020; the benefit of priority of each of which is hereby claimed herein, and which applications and publication are hereby incorporated herein by reference in their entireties.

FIELD

This disclosure relates to methods of controlling operation of radiotherapy device. In particular it relates to methods of controlling the rate of delivery of a prescribed dose, or amount, of radiation from a radiotherapy device. This disclosure further relates to optimising the control of radiation delivery, by a radiotherapy device.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus to destroy or damage, cells which form part of the tumour.

A radiotherapy device typically comprises a gantry which supports a treatment apparatus that comprises a beam generation system, or other radiation source, which is rotatable around a patient. For example, for a linear accelerator (LINAC) device, the beam generation system may comprise a source of radio frequency energy, a source of electrons, an accelerating waveguide, and beam shaping apparatus. Clinical LINAC devices are configured to deliver high energy radiation to a patient.

For the purposes of radiotherapy treatment, it is desirable to deliver a particular dose of radiation to a target region or regions, as prescribed by a treatment plan, while minimising the dose to surrounding areas of healthy tissue. Radiotherapy systems typically deliver beams of megavolt (MV) radiation energy from different angles to the area to be treated, i.e. the target region. In this way, each portion of healthy tissue surrounding the target region is only exposed to the radiation beam intermittently, at particular angles, whilst the target region is exposed to the MV radiation beam throughout treatment, at every angle.

Some radiotherapy devices, such as devices capable of performing Image Guided Radiotherapy (IGRT), include imaging capabilities. The images of a patient that are provided by an imaging apparatus may be used to assist with treatment planning and positioning of the patient. The imaging apparatus may, for example, comprise a source of kilovolt (kV) energy radiation, such as X-rays. The imaging apparatus is typically mounted on the rotatable gantry of the radiotherapy device, spatially separated from the treatment apparatus.

Radiotherapy devices are generally large, complex machines, with many moving parts and inter-operating mechanisms, requiring precision engineering and rigorous testing. Some component parts of radiotherapy machines may interact with other component parts in complex ways.

For example, the Elekta 'Unity' device is an MR-LINAC (magnetic resonance linear accelerator), which is a radiotherapy device in which the radiation beam travels through a helium-filled cryostat. The LINAC component of the Unity device can provide radiotherapy and x-ray imaging capability. The MR component of the Unity device can provide magnetic resonance imaging capability. Typically, the radiation from the LINAC will be delivered, to the patient, by travelling through (i.e. via) the cryostat of the MR apparatus. The components of the cryostat typically cause attenuation of the radiation beam, as it travels therethrough. In other words; the intensity of a radiation beam is reduced, as it travels through the cryostat. The reduction may be caused by absorption or by deflection (scatter) of photons within the beam, by the components of the cryostat. The extent of the intensity reduction may vary according to a number of factors including, for example, the energy of the radiation beam and the material of the cryostat components. The attenuation will also depend on the length of the beam's path through the cryostat. As the skilled reader will know, an 'inverse square law' applies for radiation, meaning that the dose delivery rate of the radiation beam is inversely proportional to the square of the distance from its source (i.e. from where it is output by the output by the beam generation system, in a radiotherapy device) to its point of delivery, to a patient.

Although it causes beam attenuation and thus typically outputs a radiation beam that is of a lower radiation dose rate per unit time than beams output by conventional LINACs that do not include a cryostat; an MR-LINAC such as Elekta's Unity device has other advantages that make it highly useful, such as the ability to see soft tissue and to adapt to dynamic changes, for example in movement. Nonetheless, there is an ongoing demand to further improve the efficiency and capabilities of all types of radiotherapy devices. The present disclosure relates to all types of radiotherapy device. Any particular examples described herein should be regarded as being illustrative and not to be limiting.

Regardless of the type of radiotherapy device involved, one of the main practical constraints of patient radiotherapy treatment is the availability of radiotherapy devices. Radiotherapy devices, and the radiotherapy environments in which they must be located, are typically large and expensive, and healthcare providers such as hospitals and clinics will have a limited number of them available, for treating their patients. Moreover, the provision of radiotherapy treatment has a key physical constraint in that it is generally highly inefficient, with significant heat being generated each time a radiation beam is generated and output. A radiotherapy device will therefore typically require a significant period of 'cool-down' time, between treatment applications. The cool-down time will usually coincide with a changeover time, between patients, and is often a contributory factor in determining the length (in time) of a patient appointment (or 'session') and the time intervals at which successive appointments can be scheduled. Another contributory factor is the length of time taken to deliver the required radiation to the patient, during each appointment. Any improvement in efficiencies of a radiation device, in order to reduce appointment time, and/or to reduce the spacings between consecutive appointments, and/or to reduce the number of appointments that an individual patient must attend, and thus improve patient throughput, are generally desirable.

In addition to the above; typically any course of radiotherapy treatment is delivered to the patient over a number of sessions or appointments. In terms of treatment planning, each patient session may be referred to as a 'fraction.' Treatment planning will usually include an 'inter-fraction motion management phase', to account for motions or changes of the patient's anatomy, between sessions (i.e. between different respective fractions of the treatment plan). Such motions may comprise internal anatomical motions, e.g. caused by the movement of gas or fluid inside a patient and/or motion due to anatomical processes such as respiration and blood circulation. In addition, a treatment plan may prescribe that a margin should be incorporated into the shape and size of a radiation beam that is applied to a target area, in order to account for factors such as clinical uncertainty regarding the exact size and shape of a target area, such as a tumour, and possible motion of or around the target area, during a treatment session, and thus to avoid missing any target cells.

In practice during a radiotherapy treatment session (or 'fraction'), the probability of an anatomical motion occurring, which was unaccounted for by the margin prescribed by the treatment plan and/or by an inter-fraction motion management phase, increases with time. In other words; the more time that the patient has to spend having radiotherapy treatment delivered to him or her during a radiotherapy session, the greater the chance that there will be a motion within the patient's anatomy that would, or at least could, disrupt or reduce the efficacy of the treatment. If such motion does occur, often it will trigger additional workflow steps by the clinical professional who is delivering the treatment, to account for it. Such additional workflow steps typically increase the session time, hence putting additional pressure on scheduling and patient throughput. In some instances, a clinical professional may choose to continue a radiotherapy treatment session without taking any steps to accommodate a detected anatomical motion. Whilst such a decision would be based on professional clinical judgement, it may nonetheless risk reducing the efficacy of that particular radiotherapy treatment session. The probability of the clinical professional having to make such a judgement can be reduced by reducing the delivery time for a prescribed dose (or a predetermined portion or fraction of a prescribed dose) of radiation. Therefore, reducing the delivery time would enable a treatment plan to be adhered to more closely and accurately, and would also reduce the risk of a radiotherapy session having to be extended (in terms of length of time), due to unplanned-for changes.

SUMMARY

According to an aspect, a computer-implemented method of determining a control scheme for operating a radiotherapy device for delivery of a radiation dose via a radiotherapy treatment beam to a target is provided. The radiotherapy device comprises a beam generation apparatus that is configured to output radiation via a radiotherapy treatment beam. Operation of the radiotherapy device can be described using at least one operational parameter, and the method comprises determining the control scheme by identifying a first time (t1) at which at least a first portion of the radiation dose is to be delivered at a first radiation delivery rate; and identifying a second time (t2) for the radiotherapy device to undergo a cool-down period. During the cool-down period the radiation delivery rate is less than the first radiation delivery rate. The control scheme is determined such that at least one criterion associated with the at least one operational parameter is met.

Optionally, the radiation delivery rate during the cool-down period is zero. Alternatively, the radiation delivery rate during the cool-down period may comprise a default maximum delivery rate threshold for the beam generation apparatus.

In an implementation, the device comprises a beam generation apparatus that is selectively configurable to output radiation via a radiotherapy treatment beam at either of a first non-zero radiation delivery rate or a second, lower non-zero radiation delivery rate, and a cool-down period comprises applying radiation at the second, lower non-zero radiation delivery rate, or else comprises a period of 'beam-off' in which the radiation beam is switched off.

Optionally, the first time (t1) and the second time (t2) occur within a pre-determined common time window.

Optionally, the second time (t2) is a time at which the target, or a part of the target, will exhibit a pre-determined motion characteristic. Optionally, the pre-determined motion characteristic is that the target location is such that radiation may not be safely delivered to the target at that time. This may be determined, for example, by imaging information obtained during the treatment.

Optionally, the target is subject to anatomical motion, and determining the control scheme further comprises receiving information indicative of the movement of the target with respect to a treatment volume through which the radiation treatment beam will pass; and identifying the first time (t1) such that the at least a first portion of the radiation dose is delivered while the target is at least partly located within the treatment volume; and/or identifying the second time (t2) such that the cool-down period occurs while the target is at least partly located outside the treatment volume.

In an implementation, the treatment may account for the movement of the target, for example due to the patient's respiratory or cardiac motion, by monitoring the position of the target with respect to the treatment volume. The radiotherapy device is configured to deliver radiation toward the treatment volume. Periods of relatively high dose delivery rate can be scheduled for periods of time when the target will be located within the treatment volume, and periods of relatively lower dose delivery rate can be scheduled for periods of time when the target will be located outside the treatment volume. Accordingly, the radiation dose delivered to healthy tissue can be reduced.

Optionally, the target comprises one or more target regions on or within a patient's body.

Optionally, each of the first time (t1) and the second time (t2) comprises one or any combination of: one or more instantaneous times; one or more pulse durations and one or more continuous time periods.

Optionally, the first delivery rate is determined, and/or the first time is identified, based on the at least one operational parameter of the radiotherapy device.

Optionally, the one or more operational parameter comprises any of voltage, current, power, or heat.

Optionally, the at least one criterion is that the at least one machine parameter must be kept below a threshold throughout implementation of the control scheme.

Optionally, the at least one operational parameter is associated with at least one component of the radiotherapy device, wherein the at least one component comprises any of a magnetron, an RF window, an RF circulator, a cooling system, and the beam generation apparatus.

Optionally, the at least one operational parameter is heat generated at a component of the radiotherapy device, and the at least one criterion is that a predefined heat threshold should not be exceeded.

Optionally, there is a pre-determined heat threshold for the radiotherapy device and the method further comprises determining the control scheme such that the amount of heat generated during the first time (t1) and during the cool-down period does not exceed the pre-determined heat threshold.

Optionally, a second portion of the radiation dose is delivered during the cool-down period, and determining the control scheme such that the amount of heat generated does not exceed the pre-determined heat threshold comprises ensuring that a ratio between the size of the first portion of the radiation dose and the size of the second portion of the radiation dose is in accordance with that heat threshold.

Optionally, the control scheme comprises instructions which, when implemented, cause the radiotherapy device to apply the radiotherapy treatment beam intermittently to the target, during at least part of the first time (t2).

Optionally, the radiotherapy treatment beam comprises a plurality of radiation pulses, emitted at a pulse repetition frequency (PRF), and the control scheme comprises instructions which, when implemented, cause the radiotherapy device to emit one or more radiation pulses which coincide with an occurrence of the first time (t2).

Optionally, the control scheme comprises instructions which, when implemented, cause the radiotherapy device to deliver the at least a first portion of the radiation dose at the first time and at the first delivery rate; and deliver a second portion of the radiation dose at the second time and at a second delivery rate.

Optionally, there is a pre-determined heat threshold for the beam generation apparatus, the method comprising increasing the size of the second portion, relative to the first portion, to decrease the total delivery time for the radiation dose, without exceeding the pre-determined heat threshold for the beam generation apparatus.

Optionally, determining the control scheme comprises scheduling a plurality of first times at which radiation is to be delivered at the first radiation delivery rate, and a plurality of second times at which the radiotherapy device is to undergo a cool-down period. The control scheme may be further determined such that the at least one criterion is met throughout the implementation of the control scheme.

According to an aspect, a method of controlling operation of a radiotherapy device for delivery of a radiotherapy treatment beam is provided. The beam generation apparatus is configured to output the radiotherapy treatment beam as a plurality of radiation pulses, at a pulse repetition frequency (PRF), and the radiotherapy device is selectively configurable to apply the radiotherapy treatment beam intermittently to a target, during a pre-determined time window, such that the pre-determined window comprises at least a first period of time during which the beam is applied to the target and a second period of time, during which the beam is not applied to the target. The method further comprises controlling the emission of one or more radiation pulses to coincide with an occurrence of the first period of time.

Optionally, the method further comprises controlling the emission of a radiation pulse to occur substantially at the beginning of the first period of time.

Optionally, the method further comprises increasing the pulse repetition frequency (PRF), during the first period of time.

According to an aspect, a computer program is provided, comprising instructions which, when executed by a computer, causes the computer to perform a method according to any of the methods described herein.

According to an aspect, a computer readable medium is provided, having stored thereon a computer program comprising instructions which, when executed by a computer, causes the computer to perform a method according to any of the methods described herein.

According to an aspect, a data carrier signal is provided, carrying a computer program comprising instructions which, when executed by a computer, causes the computer to perform a method according to any of the methods described herein.

According to an aspect, a data processing apparatus for a radiotherapy system is provided, the data processing apparatus comprising a processor configured to perform a method according to any of the methods described herein.

According to an aspect, a radiotherapy device for delivery of a radiotherapy treatment beam is provided. The radiotherapy device comprises a beam generation apparatus that is configured to output radiation via a radiotherapy treatment beam, and operation of the radiotherapy device can be described using at least one operational parameter. The radiotherapy device is configured to deliver a radiation dose to a target, and further comprises a processor configured to determine a control scheme according to at least one criterion associated with the at least one operational parameter. The control scheme comprises instructions which, when implemented by the radiotherapy device, cause the radiotherapy device to: deliver at least a first portion of the radiation dose at a first radiation delivery rate at a first time (t1); and undergo a cool-down period, wherein during the cool-down period the radiation delivery rate is less than the first radiation delivery rate.

FIGURES

Specific embodiments are now described, by way of example only, with reference to the drawings, in which:

FIG. 2b is a second cross-sectional view of the cryostat of FIG. 2a;

DETAILED DESCRIPTION

Figure 1:
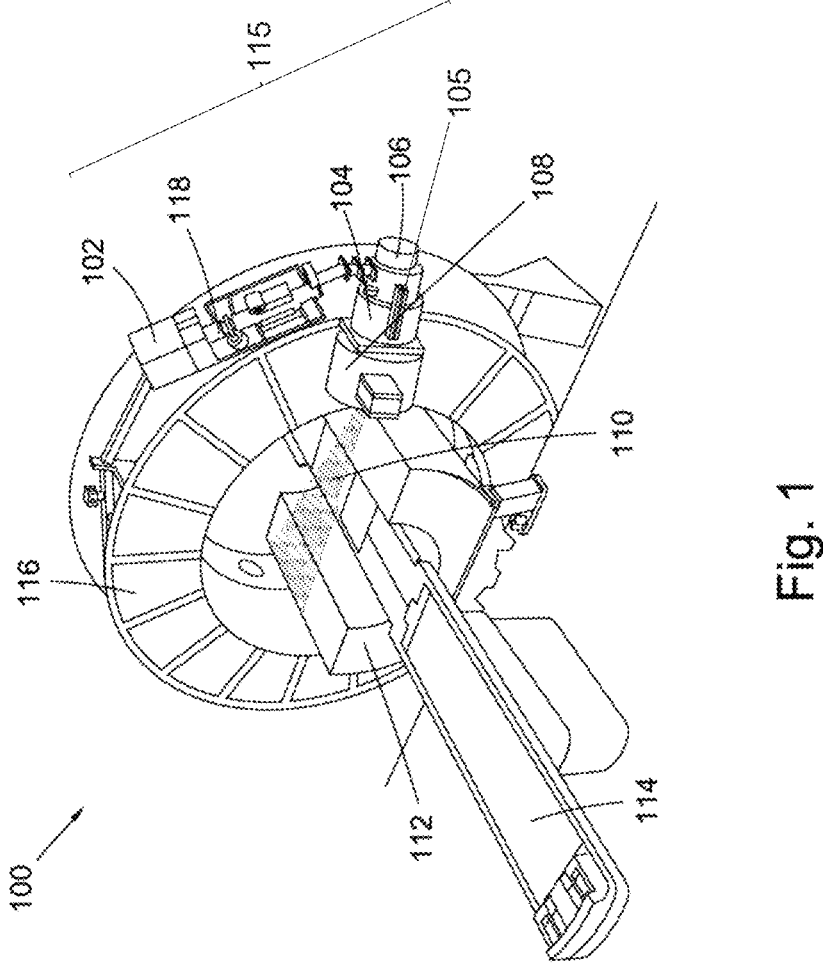
FIG. 1 is a schematic illustration of an MR-LINAC device.

Improved methods, apparatus, system and controller are provided, which enable improved control of the operation of a radiotherapy device, for delivery of a radiotherapy treatment beam. The improved control enables at least part of a pre-determined amount, or dose, of radiation to be delivered to a patient at higher intensity, and thus more efficiently and often more quickly, than is possible with conventional radiotherapy techniques. The improved control can enable optimised delivery of a dose of radiation to the patient, taking into account a plurality of contributory factors, but in particular taking into account a criterion associated with a machine operating parameter.

At the highest level, the application describes a method of controlling a radiotherapy device, in particular via determining a control scheme to be implemented by a radiotherapy device. The control scheme comprises computer executable instructions which control the delivery of radiation by the radiotherapy device. The radiotherapy device can operate in a plurality of modes, each with a different radiation delivery rate. In a first example mode, the radiation delivery rate is high; much higher than is standard for a radiotherapy device. In a second example mode, the radiation delivery rate is non-zero and lower than the delivery rate in the first mode. In a third example mode, the radiation delivery rate is zero; for this reason, this mode may be referred to as a 'beam-off' mode.

It is desirable to apply a prescribed dose of radiation at a high delivery rate, when it is safe to do so, in order to reduce the patient's overall treatment time. The different operating modes, however, may impact different operational parameters of the radiotherapy device in different ways. For example, operation of the radiotherapy device at a very high delivery rate can generate significant amounts of heat at the machine components, such as at the beam generation apparatus. It is desirable to ensure that these machine operational parameters do not exceed particular constraints during implementation of the control scheme.

The present method may therefore comprise optimising the control scheme in order to reduce treatment time, by scheduling times at which the radiotherapy device is to operate in each of its available modes of operation. The various available modes of operation have different radiation delivery rates and each impact a machine operational parameter in a different way. The scheduling may therefore be optimised to reduce treatment time, while being constrained such that a criterion associated with at least one operational parameter is met. For example, determining the control scheme may comprise identifying a first time (t1) at which at least a first portion of a radiation dose is to be delivered at a first radiation delivery rate, and identifying a second time (t2) for the radiotherapy device to undergo a cool-down period. In the cool-down period, the delivery rate is reduced when compared to the first delivery rate. The cool-down period may comprise a period of 'beam-off' operation. The first time and the start of the cool-down period are identified and scheduled such that the criterion is met. For example, the times are identified and scheduled such that a heat or power threshold will not be exceeded during implementation of the control scheme. The identification of these times may also be constrained by clinical factors, such as when it is safe to deliver radiation, for example as determined by real-time images of the target.

A computer-implemented method of determining a control scheme for operating a radiotherapy device is provided. The radiotherapy device is configured for delivery of a radiation dose via a radiotherapy treatment beam to a target. The radiotherapy device comprises a beam generation apparatus that is configured to output radiation via a radiotherapy treatment beam. Operation of the radiotherapy device can be described using at least one operational parameter, and the method comprises determining the control scheme by identifying a first time (t1) at which at least a first portion of the radiation dose is to be delivered at a first radiation delivery rate; and identifying a second time (t2) for the radiotherapy device to undergo a cool-down period. During the cool-down period the radiation delivery rate is less than the first radiation delivery rate, and may be zero or non-zero. The control scheme is determined such that at least one criterion associated with the at least one operational parameter is met.

As used herein, 'radiation dose' may be regarded as an amount of radiation. The 'dose' may also indicate one or more characteristics of the type of radiation that is to be delivered.

The first radiation delivery rate and the delivery rate delivered during the cool-down period may be referred to, respectively, as first and second radiation delivery rates or first and second radiation beam intensities. A 'delivery rate' or a 'beam intensity' as used herein may be regarded as indicating an amount of radiation delivered, via the radiotherapy treatment beam, per unit time, during the corresponding time (or, time period, or, time window), to which that delivery rate or beam intensity applies.

The beam generation apparatus may comprise one or more heat generating components. The beam generation apparatus may create heat, when it is generating a radiation beam. The amount of heat generated, per unit time, may increase as the intensity (or, delivery rate) of the radiation beam increases. The heat generation may comprise instantaneous heating and/or average heating, over a period of time.

The second radiation delivery rate may comprise a default delivery rate for the beam generation apparatus. The radiotherapy device may be configured to default to delivering radiation at the second radiation delivery rate, at a time or times at which the method according to any of the present aspects is not being carried out.

When the machine is delivering radiation at the first delivery rate, machine operating parameters are affected differently than when the machine is delivering radiation at the second delivery rate. For example, typically, more power is required when delivering radiation at the first (higher) delivery rate, more heat is generated at the beam generation system, and more energy is passing through the RF windows in the RF system causing them to heat up. Periods of time in which radiation is delivered at the second delivery rate can be described as 'cool-down' periods, in part because the machine operational parameters are reduced during these periods. For example, less heat is generated, and less power is required to maintain the second radiation delivery rate.

The second delivery rate may comprise a default maximum delivery rate threshold for the beam generation apparatus. The radiotherapy device may be configured to default to delivering radiation at a delivery rate that does not exceed the maximum delivery rate threshold, at a time or times at which the method according to any of the present aspects is not being carried out.

The first delivery rate and/or the default delivery rate and/or default maximum delivery rate threshold may be predetermined, for the radiotherapy device, based on one or more factors that may include safety considerations and/or thermal properties of one or more components of the radiotherapy device. The first delivery rate and/or the default delivery rate and/or default maximum delivery rate threshold may be predetermined based on a set of assumptions, regarding operation of the radiotherapy device. The set of assumptions may include an assumption of continuous, steady-state operation of the beam generation apparatus over an extended period of time. A buffer or safety margin may be provided, between a magnitude of the first delivery rate and/or the default delivery rate and/or default maximum delivery rate threshold that is permissible, according to the factors considered and set of assumptions adopted, and a magnitude of the first delivery rate and/or the default delivery rate and/or default maximum delivery rate threshold that the radiotherapy device is actually configured to provide.

The second delivery rate may be predetermined, for the radiotherapy device, based on one or more factors that may include safety considerations and/or thermal properties of one or more components of the radiotherapy device. The second delivery rate may be predetermined based on a set of assumptions, regarding operation of the radiotherapy device. The set of assumptions that are used to predetermine the second delivery rate may be at least partially different to the set of assumptions that are used to predetermine the first delivery rate. The second delivery rate may be predetermined based on one or more operational parameters for the radiotherapy device. The one or more operational parameters may include an intended or required treatment plan, which the radiotherapy device is required (or, intended) to delivered to a patient. The one or more operational parameters may include known operating patterns for the radiotherapy device, such as a pre-set minimum gap between patient treatment sessions and/or known operating hours of the radiotherapy device, within a day or other time period. The second delivery rate may be predetermined based on operational behaviour that has been observed or learnt for the radiotherapy device, or for one or more similar radiotherapy devices. For example, that operational behaviour may include one or more relationships between any of: intensity of radiation delivered, one or more patterns of radiation delivery, length (in units of time) of radiation delivery, and heating effects.

The radiotherapy device/system comprises multiple components, for example those components described herein with respect to FIG. 1. For example, the components may include a magnetron, an RF window, an RF circulator, a cooling system, and the beam generation apparatus. Each of these components is associated with one, or several, operational parameters, which must be managed to ensure optimised operation of the system. Examples of these operating, or operational, parameters include the power applied to the magnetron and electron gun, other electrical quantities associated with the operation of the magnetron and electron gun such as the current and voltage, the power of RF passing through RF windows and circulators in the RF system, and the heat being generated by, at, or nearby any of these components. Some of these operational parameters have static design constraints associated with them that can be predefined. Others, such as ordering of beams to optimise cooling, will depend on the planned delivery/treatment.

The present inventors have appreciated that controlling radiotherapy treatment according to these operational parameters, and in particular determining durations at which a plurality of different radiation delivery rates should be applied based on these operational parameters, is beneficial for several reasons. In an example, the operational parameter(s) may relate to the heat being generated by the various components of the radiotherapy device. As described elsewhere herein, controlling operation of the radiotherapy device such that a high or maximal dose is applied to the target while ensuring that a heat threshold for the radiotherapy device is not exceeded allows for improved efficiency of treatment, reduced treatment time, and greater patient throughput, all while ensuring the device's operational parameters are kept within safe limits.

In an example according to the present disclosure, operation of the radiotherapy device can be described using at least one operational parameter, and the radiotherapy can be controlled (or, equivalently, a control scheme for the device can be determined) such that at least one criterion associated with the at least one operational parameter is met. One way the radiotherapy can be controlled to ensure the criterion is met is to determine the second delivery rate, and/or to identify the second time at which a cool-down period should be applied, based on the at least one operational parameter of the radiotherapy device. For example, the higher delivery rate, and the time during which it should be applied, can be controlled such that a heat criterion is not exceeded during radiotherapy treatment.

The operational parameters need not relate to the heat generated by, at, or near the components of the radiotherapy device. For example, the magnetron will have certain power limitations which should not be exceeded. It is similarly possible to control operation of the radiotherapy device such that a high or maximal dose is applied to the target, while ensuring that the magnetron's power limitations are not exceeded. Similarly, the durations at which different dose rates are applied can be controlled according to power constraints of the RF window(s) in the RF system.

Basing a control scheme for a radiotherapy device on the device's operational parameters in this way, and in particular identifying a first time at which a first portion of a radiation dose is to be delivered at a first radiation delivery rate and identifying a second time (t2) at which the device is to undergo a cool-down period based on the operational parameters of the device, increases the speed and efficiency of treatment while ensuring the device continues to operate safely.

In a device comprising a beam generation apparatus that can output treatment beams at a plurality of delivery rates, the method may comprise determining any of the following: i) a first delivery rate to be used, ii) a second delivery rate to be used, iii) a first time during which the first delivery rate is to be used; and iv) a second time at which the second delivery rate is to be used; or any combination of these four factors. One or more of these factors may be determined based on one or more operational parameters of the radiotherapy device.

Controlling the times during which the first (higher) rate is applied, e.g. by interspersing periods during which the higher rate is applied with periods in which the second (lower) rate is applied such that the machine's operational parameters are kept within an operating constraint, is beneficial, as applying the beam at the higher delivery rate typically puts more strain on the device. For example, when the beam generation apparatus is delivering radiation at the higher delivery rate, more power is being applied to the magnetron, and more heat is being generated by the beam generation apparatus.

A control scheme for the device can be determined, in which application of radiation at the various available delivery rates is scheduled such that a machine operating parameter is kept under a certain level. For example, determining the control scheme may comprise scheduling a plurality of first times at which radiation is to be delivered at the first radiation delivery rate, and a plurality of second times at which the radiotherapy device is to undergo a cool-down period during which a lower or even a zero rate is applied. The times are scheduled such that the machine operating parameter is kept under the certain level throughout implementation of the control scheme.

Generally, the method can comprise determining any of the four factors above, and in particular the times at which different radiation delivery rates should be applied, based on at least one criterion relating to the one or more operational parameters of the radiotherapy device. The control scheme may be determined such that a constraint associated with the operational parameters of the radiotherapy device is not exceeded. The criterion may be a heat generation criterion, such that the method comprises controlling one or more of the four factors such that a heat generation threshold is not exceeded. The criterion may be a power criterion, such that the method comprises controlling one or more of the four factors such that the power supplied to a particular component of the device, such as a magnetron, electron gun, or the like, does not exceed a power threshold. It should be appreciated that operational parameters may comprise any of voltage, current, power, heat, and the associated components may be any of the components described herein, such as a magnetron, an RF window, an RF circulator, a cooling system, and the beam generation apparatus.

The cool-down period may comprise a zero delivery rate, i.e. a period of 'beam-off'. Each of the first time (t1), at which at least a first portion of the radiation dose is to be delivered at a first radiation delivery rate, and the second time (t2) during which a cool-down period is to be applied, may comprise one or any combination of: one or more instantaneous times; one or more pulse durations and one or more continuous time periods. Each of the first time (t1) and the second time (t2) may comprise a respective plurality of instantaneous times or pulse durations or continuous time periods (or, time windows).

The target may comprise one or more target regions on or within a patient's body. A period of beam-off may comprise a transition time between treating a first target region and a second target region, or else may comprise a time during which the tumour is not located at an optimal position for treatment.

There may be one or more pre-determined heat thresholds for the radiotherapy device. The device may be configured to deliver a first portion of a prescribed dose at the first delivery rate, and a second portion of the dose at the second delivery rate. In this implementation, the method may comprise controlling operation of the radiotherapy device to ensure that a ratio between the size of the first portion of the radiation dose and the size of the second portion of the radiation dose is in accordance with the heat threshold. The ratio may be determined so that the amount of heat generated, either at an instant and/or over a period of time, by generating radiation at the first beam delivery rate during the first time (t1) and generating radiation at the second beam delivery rate during the second time (t2) does not exceed one or more of the pre-determined heat thresholds.

The target may be subject to anatomical motion. The start of the cool-down period may be a time at which the target, or a part of the target, will exhibit a pre-determined motion characteristic. For example, the second time (t2) may comprise a time at which the target, or part of the target, or fluid or gas near the target, is moving, such that radiation may not be safely deliverable to the target at that time.

The radiotherapy treatment beam may be intermittently applied to a target, during at least part of the first time (t1). For example, it may be a gated beam delivery, for example to a target that is subject to anatomical motion, for example periodic motion such as respiration.

Respiratory and cardiac gating allows for a treatment volume to be defined. In treatment which involves respiratory or cardiac gating, radiation is only applied when the target, or part of the target, is located within this predefined treatment volume. Radiation can be 'switched off' while the target is located outside the treatment volume. In this way, treatment is optimised, in part by reducing the radiation dose applied to healthy tissue.

The treatment volume may be referred to as a gating volume, or a treatment field. As the patient breathes, their internal anatomy moves according to their respiratory cycle.

Similarly, as the patient's heart beats, their internal anatomy moves according to their cardiac cycle. It is possible to plan to deliver radiation only at particular parts of the patient's respiratory and/or cardiac cycle which correspond with the target, e.g. a tumour, being located at an optimal position for treatment. For example, it may be determined that radiation should be applied only during the mid-points of the patient's respiratory cycle, and not near the turning points of the cycle.

Where the target is subject to anatomical motion, the second time (t2), i.e. the commencement of a cool-down period, may be a time at which the target, or a part of the target, will exhibit a pre-determined motion characteristic. For example, the anatomical motion may be such that the target, or a part of the target, is regularly brought in to, and out from, a treatment volume. The treatment volume is a volume through which the radiation beam will pass during treatment. The treatment volume can be determined by clinicians based on the patient's anatomy and clinical considerations. It is beneficial to plan cool-down periods, i.e. periods of lower or zero radiation delivery rate, for times at which the target will be located wholly or partly outside the treatment volume.

Similarly, it is beneficial to apply radiation at the higher dose rate when the target, or part of the target, is located within the treatment volume. Therefore, the first time may be identified, i.e. planned, such that the higher delivery rate is delivered while the target is wholly or partly within the treatment volume.

The radiotherapy treatment beam may comprise a plurality of radiation pulses, emitted at a pulse repetition frequency (PRF), the method further comprising controlling the emission of one or more radiation pulses to coincide with an occurrence of the second time (t2). For example, one or more radiation pulses may be controlled to coincide with the start of the second time (t2), when the second time (t2) comprises a time window or a time pulse which has a pulse width.

In implementations in which the radiation delivery rate is non-zero during the cool-down period, it is possible to swap between the two non-zero radiation delivery rates to deliver a prescribed dose. For example, a first portion of the radiation dose can be scheduled to be delivered at the first time and at the first delivery rate, and a second portion of the radiation dose can be scheduled to be delivered at the second time and at the second delivery rate. The method may therefore comprise adjusting the size of the second portion, relative to the first portion, to decrease the total delivery time for the radiation dose as far as possible, without exceeding the pre-determined heat threshold for the beam generation apparatus.

High-Level Overview of an MR-LINAC

FIG. 1 depicts a radiotherapy device 100 that is suitable for delivering, and configured to deliver, a beam of radiation to a patient during radiotherapy treatment. The device 100 depicted in FIG. 1 is suitable for being controlled (and/or modelled) as described herein. While the device 100 in FIG. 1 is an MR-LINAC, this is by way of example only and should not be regarded as limiting. The present disclosure may be applied to any radiotherapy device, for example a LINAC device.

The device 100 depicted in FIG. 1 is an MR-LINAC. The device 100 comprises an MR imaging apparatus 112 and a radiotherapy (RT) apparatus, which may comprise a LINAC device. In operation, the MR imaging apparatus 112 produces MR images of the patient, and the LINAC device generates and shapes a beam of radiation and directs it toward a target region within a patient's body in accordance with a radiotherapy treatment plan. The radiotherapy/LINAC aspect of the device 100 may also be capable of capturing images. The device 100 depicted in FIG. 1 is shown without a cover or 'housing', which would cover the MR imaging apparatus 112 and RT apparatus in a commercial setting such as a hospital or clinic.

The RT apparatus within the MR-LINAC device 100 of FIG. 1 comprises beam generation equipment, including: a source of RF waves 102, a circulator 118, a source of electrons such as an electron gun, a waveguide 104, and a target, such as a tungsten target. The target (or a component enclosing the target) is referred to herein as being the 'radiation source' 106, since it emits a radiation beam 110 towards the patient. Thus, as shown in FIG. 1, the beam generation equipment or components (the source of RF waves 102, the waveguide 104, the circulator 118, etc.,) collectively form a beam generation apparatus 115 of the radiotherapy device 100. The RT apparatus also comprises a collimator 108, such as a multi-leaf collimator, configured to collimate and shape the radiation beam 110.

The MR-LINAC includes a patient support surface 114 and a ring-shaped gantry 116 which, in combination with the housing (not shown), defines a substantially central opening, or 'bore'. The patient support surface 114 is moveable and can be used to move a patient, or other subject, in and out of the bore for MR scanning and/or radiotherapy imaging or treatment. The MR imaging apparatus 112, the RT apparatus, and an actuator, arranged for actuating the patient support surface 114, are communicatively coupled to one or more controllers or processors (not shown). The controller(s) is/are also communicatively coupled to a memory device comprising computer-executable instructions, which may be executed by the controller. As the skilled reader will be aware, not all types of radiotherapy include a bore and, in some cases, a patient support surface may not be moveable, or at least not in the same way as described herein in relation to FIG. 1. Any such description is therefore to be regarded as illustrative only, and not limiting.

The RT apparatus also comprises a radiation detector (not shown). Typically, the radiation detector is positioned diametrically opposite the radiation source 106, on the gantry 116. The radiation detector is suitable for, and configured to, produce radiation intensity data. In particular, the radiation detector is positioned and configured to detect the intensity of radiation which has passed through the subject (i.e. the patient). The radiation detector may also be described as radiation detecting means.

The radiation detector may form part of a portal imaging system. It may comprise an imaging device, which may be positioned on the gantry 116, diametrically opposite the radiation source 106, from which the radiation beam 110 is emitted, and can be used to image the therapeutic radiation produced by the LINAC during radiotherapy treatment. The imaging device may be a digital imaging device such as a CCD camera, or another semiconductor-based detector, and/or a liquid ion chamber. The imaging device may be a megavoltage X-ray imager and/or an electronic portal imaging device (EPID). The imaging device may comprise a flat panel detector, a scintillator, an a-Si based image panel, and/or a scintillator-mirror-camera system. References to EPID-based methods and apparatus within this disclosure should be considered to also apply to megavoltage X-ray imaging devices or any other appropriate imaging device.

The beam generation system, including the radiation source 106, is attached to the rotatable gantry 116 so as to rotate with the gantry 116. In this way, the radiation source 106 is rotatable around the patient so that the radiation beam 110, which is emitted by the radiation source 106, can be applied from different angles around the gantry 116. The radiation source 106 defines the point (i.e. the location, on a circumference defined by the gantry, around the patient) at which the radiation beam 110 is introduced into the bore. In a preferred implementation, the gantry 116 is continuously rotatable. In other words, the gantry 116 can be rotated by 360 degrees around the patient, and in fact may continue to be rotated past 360 degrees. The gantry 116 may be ring-shaped. In other words, the gantry 116 may be a ring-gantry.

The source 102 of radiofrequency (RF) waves, such as a magnetron, is configured to produce RF waves that are typically of a very high frequency, for example of the order of several Gigahertz (GHz). The source 102 of RF waves is coupled to the waveguide 104 via the circulator 118, and is configured to output RF waves into the waveguide 104. The source 102 is configured to provide a pulsed output of discrete pulses (or, 'packets', or, 'bursts') of RF waves, at a repetition rate that is known as a Pulse Repetition Frequency (PRF). Each pulse has a pulse width (in units of time). The RF waves may pass from the source 102 of RF waves through an RF input window and into an RF input connecting pipe or tube.

A source of electrons 105, such as an electron gun, is also coupled to the waveguide 104 and is configured to inject electrons into the waveguide 104. In the source of electrons, electrons are thermionically emitted from a cathode filament as the filament is heated. The temperature of the filament controls the number of electrons injected. The number of electrons injected may additionally be controlled by a gate voltage. In order to optimise operation of a radiotherapy device for a particular PRF (and pulse width) of the RF source 102, the injection of electrons into the waveguide 104 may be synchronised with the pumping of the RF waves into the waveguide 104. The design and operation of the RF wave source 102, electron source 105 and the waveguide 104 is such that the RF waves accelerate the electrons to very high energies as the electrons propagate through the waveguide 104.

The exact design of the waveguide 104 depends on whether the LINAC accelerates the electrons using a standing wave or a travelling wave. The waveguide 104 typically comprises a series of cells or cavities, each cavity connected by a hole or 'iris' through which the electron beam may pass. The cavities are coupled in order that a suitable electric field pattern is produced which accelerates electrons propagating through the waveguide 104.

To ensure that propagation of the electrons is not impeded as the electron beam travels toward the target, the waveguide 104 is evacuated. Electrons can be accelerated to speeds approaching the speed of light in the evacuated waveguide 104.

The radiation source 106 is configured to direct a beam 110 of therapeutic radiation toward a patient positioned on the patient support surface 114. The radiation source 106 may comprise a heavy metal target, such as a tungsten target, towards which the high energy electrons exiting the waveguide are directed. When the electrons strike the target, X-rays are produced in a variety of directions. A primary collimator 108 may block X-rays travelling in certain directions and allow only forward-travelling X-rays to pass through, producing a treatment beam 110. The X-rays may be filtered and may pass through one or more ion chambers for dose measuring. The beam can be shaped in various ways by beam-shaping apparatus, for example by using a multi-leaf collimator 108, before it is directed towards a target region in or on the patient's anatomy, as part of radiotherapy treatment.

In some implementations, the radiation source 106 is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the LINAC. Although the present disclosure uses examples comprising X-ray beams, the improved methods, devices, and/or systems disclosed herein may also be applied to electron beam arrangements. However, the generation of electron beams typically generate less heat than X-ray generation, which may limit the applicability of the methods disclosed herein to electron beam arrangements, in practice.

The radiotherapy device 100 depicted in FIG. 1 also comprises MR imaging apparatus 112. The MR imaging apparatus 112 in FIG. 1 is annular, but is shown in cross section, with only the lower half being fully visible and just an outline of the upper half being visible. The MR imaging apparatus 112 is configured to obtain images of a subject positioned, i.e. located, on the patient support surface 114. The MR imaging apparatus 112 may also be referred to as the MR imager. The MR imaging apparatus 112 may be a conventional MR imaging apparatus, operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by a controller, comprised within and/or communicatively coupled to the radiotherapy device 100.

The controller comprises one or more of: a computer, a processor, or another processing apparatus. The controller may be formed by several discrete processors; for example, the controller may comprise an MR imaging apparatus processor, which controls the MR imaging apparatus 112; an RT apparatus processor, which controls the operation of the RT apparatus; and a subject support surface processor which controls the operation and actuation of the subject support surface. The controller is communicatively coupled to at least one memory, which may comprise a computer readable medium.

As is well known to the skilled person, an MR-LINAC device, such as that depicted in FIG. 1, also comprises several other components. The whole device is cooled by a water cooling system (not shown in the figures). The water cooling system may be used, in particular, to cool the waveguide 104, target, and RF source 102. In order to ensure the LINAC does not leak radiation, appropriate shielding (not shown in the figures) is also provided.

Figure 2A:
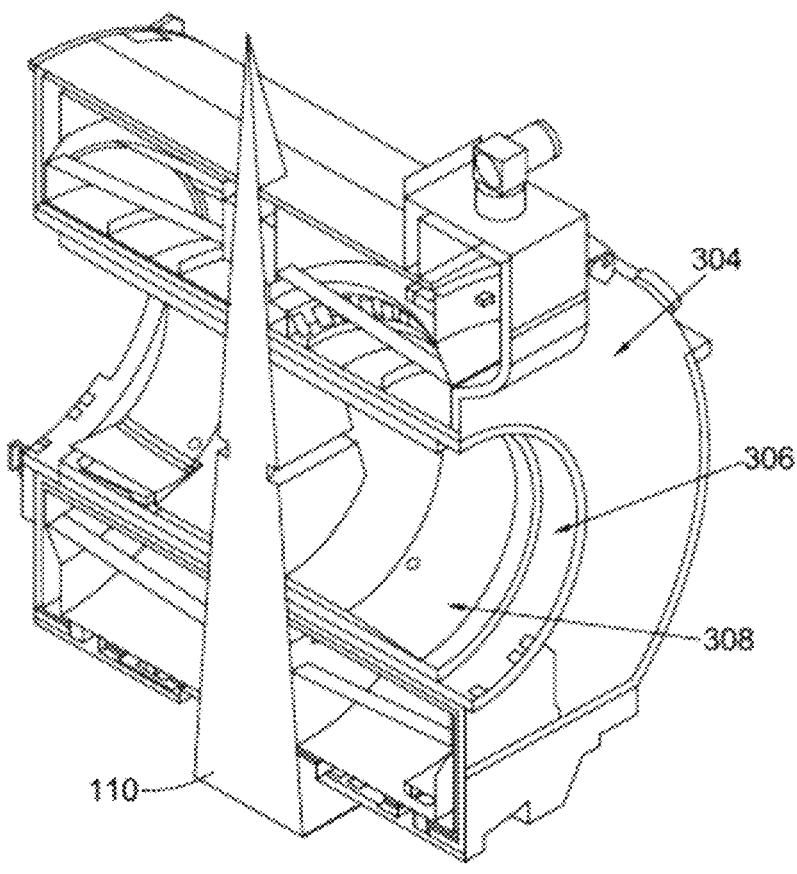
FIG. 2a is a first cross-sectional view of a cryostat.
Figure 2B:
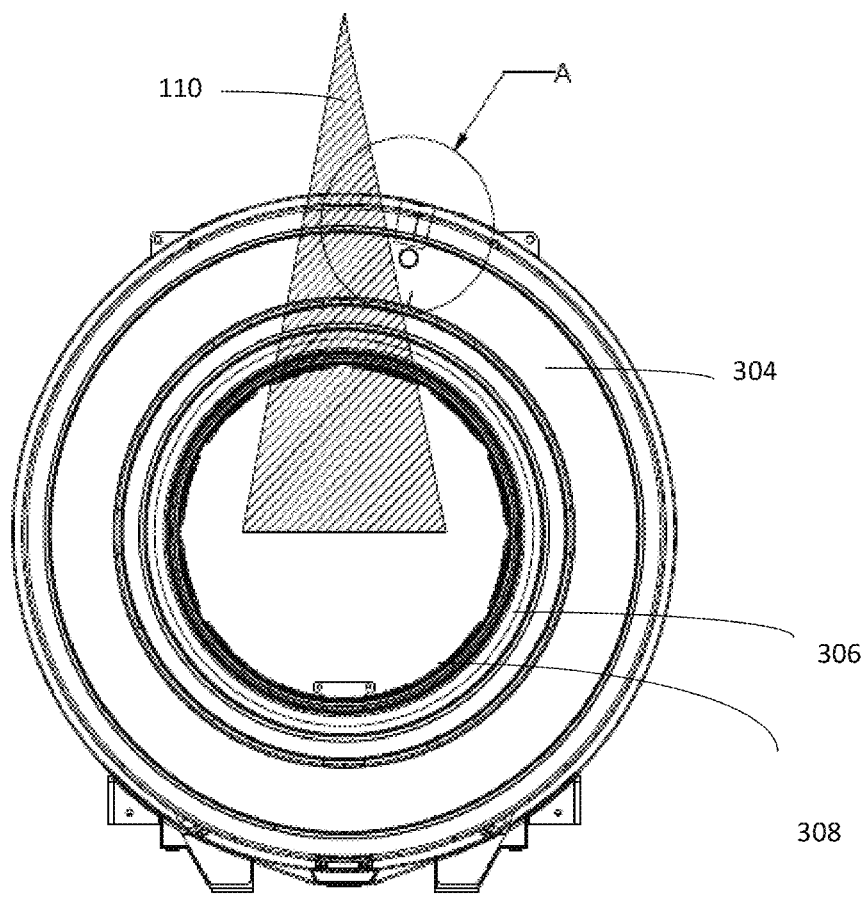

The MR imaging apparatus 112 includes a field generation unit, which is shown in cross section in FIG. 2A and FIG. 2B herein. The field generation unit comprises a cryostat 304, a gradient coil 306, and a system body coil 308. The system body coil 308 may be a quadrature body coil. As used herein, the general term 'cryostat' may be used to refer to the overall field generation unit comprising the cryostat 304, the gradient body coil 306, and the system body coil 308, any other appropriate refrigerant unit, and/or any other attenuating element. The 'cryostat' may be toroidal or cylindrical and may surround the patient during treatment. The cryostat may be fixed in position, with the gantry 116 encircling the cryostat and thus being free to rotate fully, around the bore, in order to deliver radiation from different angles. Such an arrangement means that at any given position, a radiation beam that is output by the radiation source 106 will have to pass through the cryostat, before reaching the patient. As the skilled reader will appreciate, the radiation beam will be attenuated—i.e. its intensity will be reduced—by the components of the cryostat. This being the case, the intensity (at the patient's location and/or when detected by a radiation detector, after having passed through the patient's anatomy) of a radiation beam delivered to a patient by an MR-LINAC will typically be lower than the intensity of a radiation beam that is output by a conventional LINAC, in which the radiation beams travels through air, between the radiation source and the patient.

As mentioned above; the present disclosure is not limited to MR-Linacs, but also may be applied to conventional LINACs and other types of radiotherapy devices. As the skilled reader will know; a conventional LINAC has the same (or similar) component parts as the MR-LINAC described above, with the cryostat and the MR imaging apparatus 112 omitted.

Typically, when a radiotherapy device is manufactured and configured for use (for example, by the manufacturer or by a programmer or set-up engineer), the device is configured to output radiation at a predetermined intensity—or, at a predetermined 'dose rate'—which dictates the predetermined amount of radiation that the device can deliver per unit time. As the skilled reader will understand, the dose rate is a measure of how much radiation will be actually delivered to the patient, per unit time—the radiation source will output radiation at a higher intensity than that, which will be attenuated as it travels, before being delivered to the patient. For an MR-Linac, the attenuation as the beam travels through the cryostat can be significant. For a conventional radiotherapy device, without a cryostat, for example a conventional LINAC, the attenuation between the radiation source and point of delivery is much less significant, and so the intensity of the radiation that is delivered to the patient is likely to be higher for a conventional Linac or radiotherapy device than it is for an MR-Linac.

The predetermined intensity at which a radiotherapy device is configured to deliver radiation—or, at least, a maximum upper limit of intensity, at which a radiotherapy device is configured to deliver radiation—is usually pre-set as a default operating condition of the device, and generally cannot be altered by the user—i.e. by the operator of the radiotherapy device. This is, at least in part, to aid simplicity of use for the operator, particularly if multiple operators are to use the same device and/or if an individual user may need to operate two or more radiotherapy devices (at different respective times) of the same type. Setting a default radiation intensity can also streamline radiotherapy treatment planning. A default radiation intensity may also ensure that the radiotherapy device will be operable to provide consistent treatment capability over an operating lifetime, which might be, for example, ten years.

The magnitude of the predetermined intensity (or, the magnitude of the predetermined maximum upper limit of intensity) at which a radiotherapy device is configured to deliver radiation may be determined by a number of different factors. Safety will typically be a critical consideration, for example ensuring that the heat-generating components of the device do not overheat, and that heating effects do not cause damage to any parts of the device.

As described above and as known to the skilled reader; radiation is generated and delivered, by a radiotherapy device, in pulses. The pulses of a certain width are triggered at a Pulse Repetition Frequency (PRF), which is determined by the PRF of the magnetron or other RF source. Every pulse of radiation will generate an amount of heat. The heat that is generated by the generation of each pulse of radiation has two temporal elements—pulse heating and average heating. Pulse heating may be described as an instantaneous heating effect, which occurs each time a pulse is generated. For example, pulse heating may pose a risk of a target, such as a tungsten target, cracking if it overheats quickly, when an electron beam hits it. Average heating may be described as the heating that occurs over a longer period, for example from start to end of a radiation generation session, or over the course of several hours, days, weeks, months and so on. For example, excessive average heating may lead to the cells of a waveguide within a radiotherapy apparatus developing potentially dangerous hotspots. Safety rules, and a demand to maintain consistent and reliable performance of a radiotherapy device over an extended period of time, will generally demand that both pulse heating and average heating are controlled and kept below certain thresholds.

Therefore, the predetermined intensity (or, the predetermined maximum upper limit of intensity) at which a radiotherapy device is configured to deliver radiation may be determined, at least in part, by the thermal characteristics of one or more components of a radiotherapy device, and in particular by the constraints of controlling both pulse heating and average heating. Another competing constraint however will typically be the demand for efficiency, and therefore for as much radiation to be delivered per unit time as is safely permissible.

Conventionally, average heating is controlled in order to prevent, or at least to control and manage, the risk of heat damage to components of the radiotherapy device. However, the present inventor has recognised that the calculation, and thus the control and management, of average heating for radiotherapy devices is conventionally based on an assumption of continuous, steady operation (and, therefore, of continuous, steady average temperature generation) over much longer periods of time than any radiotherapy device would typically be operating for, in practice. The inventor has further recognised that, even within each treatment session, during which radiotherapy treatment is delivered to a patient, an assumption of continuous, steady state operation is rarely accurate. In other words, the present inventor has recognised that, in practice, radiotherapy treatment is not delivered by a radiotherapy device all day long, and possibly not every day of the week, because a hospital or other radiotherapy provider will have limited operating hours, due to practicalities such as staff availability and patient convenience. Moreover, even during operating hours, the radiotherapy provider will not be delivering radiotherapy to patients at all times. Instead, there will be time between successive appointments, to enable the radiotherapy environment to be reset for the next patient. Even within a patient appointment (or 'session'), the radiotherapy will not be delivered all the time because there is time taken up by patient positioning, and possibly by other steps such as image capture, and so on. The present inventor has further recognised that, even during a period in which radiotherapy treatment is being delivered, there are circumstances in which the beam will be gated—i.e. repeatedly switched on and off—such that radiation, and therefore heat, will not be generated continuously.

The present inventor has further recognised that, although it is conventional for there to be a predetermined 'default' intensity (and/or a 'default' maximum upper intensity limit) at which a radiotherapy device is configured to deliver radiation, a radiotherapy device will typically be capable of outputting radiation at a higher intensity than the default intensity (and/or, above 'default' maximum upper intensity limit), at least in some circumstances. For example, if a radiotherapy device is operable to provide both dynamic and static radiotherapy treatment, and if a default intensity (or default maximum intensity) is calculated based on what radiation intensity the device is capable of providing during dynamic treatment, in practice the device is likely to be capable of providing a higher intensity of radiation than the default intensity (or default maximum intensity), at least during static treatment.

Therefore the present inventor has recognised that it is possible to control a radiotherapy device more efficiently. In general terms, this may be done by applying an inherent (or over-arching) 'average' thermal model, but identifying opportunities within that model in which shorter term delivery can be optimised—preferably, in which radiation delivery rate (which may also be referred to herein as 'radiation intensity') can be temporarily increased above an average or default rate (i.e. above an average or default intensity)—whilst, at the same time, preventing thermal damage to the components of the radiotherapy device.

As the skilled reader will be aware, dynamic radiotherapy techniques already exist, in which a radiation source is continually moved, relative to patient support surface, during application of the radiotherapy beam. An example of dynamic radiotherapy is VMAT (volumetric modulated arc therapy), which is a type of IMRT (intensity modulated radiotherapy). In VMAT, the radiotherapy machine rotates around the patient, in an arc shape, during application of the radiotherapy beam. The radiotherapy device (and/or its controller) can be configured, in VMAT, to reshape and/or to change the intensity of the radiation beam, as it moves around the body. Therefore, the dose rate in VMAT can differ, between different respective treatment segments (i.e. between different respective angular positions of the radiotherapy beam source, relative to the patient). However, the available dose rates for VMAT—and the maximum allowable dose rates—are conventionally calculated based on a similar set of assumptions to those on which the calculation of default/maximum intensities for static radiotherapy delivery are based. Therefore, the present inventor has also recognised that it is possible to control a radiotherapy device more efficiently, even for dynamic radiotherapy treatment, in which some variation in available beam intensity already exists.

An improved method, and device and/or system, is therefore provided herein, for controlling operation of a radiotherapy device for delivery of a radiotherapy treatment beam. The methods disclosed herein may be implemented using the radiotherapy device 100 of FIG. 1, in other words, the radiotherapy device 100 may be configured to perform the methods disclosed herein. According to the improved method, instead of being pre-configured to always output radiation at the same 'default' delivery rate (i.e. at the same default intensity of radiation), the radiotherapy device is pre-configured to be operable to selectively output radiation at either a lower delivery rate, which may be a default radiation delivery rate, or at a higher radiation delivery rate, wherein the higher radiation delivery rate is higher than the lower radiation delivery rate. In other words, the intensity of the delivered radiation will be greater (i.e. more radiation will be delivered, per unit time), when the radiation is being delivered at the higher radiation delivery rate, as compared to when radiation is being delivered at the lower radiation delivery rate.

According to the improved method; a radiation dose, or amount, which is to be delivered to a target (in or on a patient's anatomy), is determined. For example, the radiation dose may be determined from a pre-existing prescription or from a pre-existing treatment plan, or it may be calculated as part of a treatment planning process, for example based on the results of images obtained and/or tests carried out, in relation to the patient and their target region (or regions). The improved method comprises identifying a first time (t1), or times, at which a first portion, or first group of portions, of the radiation dose is to be delivered, at the higher radiation delivery rate, and identifying a second time (t2), or times, at which a second portion, or a second group of portions, of the radiation dose is to be delivered, at the lower radiation delivery rate. The first (t1) and second (t2) times may each comprise instantaneous times or time windows.

In order to increase the intensity of radiation delivery for the first time (t2), a radiotherapy device may be controlled to increase the pulse width of one or more radiation pulses, which are delivered at/during the first time (t2). Alternatively, or additionally, in order to increase the intensity of radiation delivery for the first time (t2), a radiotherapy device may be configured to increase the PRF—i.e. to increase the radiation pulse repetition rate—at which the radiation pulses are delivered at/during the first time (t2). Different approaches may be appropriate for different respective circumstances. In general, a larger amount of radiation will be delivered, per unit time, at/during the first time (t2) than at/during the second time (t1).

It is possible that the radiotherapy device will be pre-configured to be able to output radiation at more than two respectively different radiation delivery rates. For example, the radiotherapy device may be operable to output radiation at three or more respectively different radiation delivery rates. For example, the radiotherapy device may be operable to output radiation at any rate (or intensity) that lies within a predetermined range, or that is below a predetermined maximum intensity threshold. For example, the radiation delivery rate or rates that are available for a radiotherapy device may vary on a case-by-case basis. For example, the radiation delivery rate or rates that are available for a radiotherapy device may depend on a number of factors such as the amount of radiation that has been prescribed for a patient, and/or on the nature or location of the target area or areas, and/or on the number of fractions or sessions over which the radiotherapy is to be distributed, and/or on the length of available session (or fraction) time.

The present inventor has recognised that increasing the delivery rate, or intensity, of the radiation being delivered by a radiotherapy device is likely to increase heat generation, within the device. However, they have also recognised that it can still be possible to increase radiation delivery rate, or intensity, whilst adhering to safety standards and not risking excessive heating, if the circumstances under which a higher radiation delivery rate is used are intelligently selected and controlled.

For example, the present inventor has recognised that the levels of 'average heating' that are actually experienced by components of a radiotherapy device, during a radiotherapy session, may be below a permissible average heating threshold if one or more periods of relatively high intensity radiation delivery, within that session, are followed by, or otherwise combined with, one or more periods of relatively low intensity radiation delivery, within that session. A period of relatively low intensity radiation delivery may be referred to as being a 'cool-down' period for the radiotherapy device. A cool-down period might comprise a period of time in which radiation is not being generated by the radiotherapy device, and/or it may comprise a period of time in which radiation is being generated only intermittently, and/or it may comprise a period of time in which radiation is being generated at a relatively low level, thus creating a relatively small amount of heat.

For example, a period of relatively low intensity radiation delivery might comprise a period of time during which the radiation delivery rate reverts back to a lower rate, which might be a default rate or might be below a default rate.

For example, a period of relatively low intensity radiation delivery might comprise a period of time during which the beam will be switched off or paused. Therefore, according to the present disclosure, a selection may be made to increase the radiation delivery rate (i.e. to increase the beam radiation intensity) just before the end of a radiotherapy session, since the beam will naturally be switched off when the session ends, to accommodate the time taken for one patient to leave the radiotherapy environment and the next patient to arrive, plus in most cases some intervening time, during which the radiotherapy environment will be prepared for the next patient.

In another example according to the present disclosure, a period of relatively low intensity radiation delivery might comprise a period of time during which the beam is to be switched off, or paused, temporarily, during a 'transition time', within a radiotherapy treatment session. For example, if a patient's anatomy comprises more than one target region, the patient and/or the patient support surface and/or other aspects of a radiotherapy environment may have to be moved or reconfigured, when transitioning between treating a first target region and treating a second target region. That transition time might provide a cool-down period. Therefore, a period of time before the transition time might be identified as an opportunity for relatively high intensity radiation delivery.

For example, a period of relatively low intensity radiation delivery might comprise a period of time during which the beam is to be 'gated', and therefore will be intermittently switched off for part of that period of time, thus providing a relatively low average intensity of radiation delivery, over that period of time. In such a case, a period of time before the gated delivery period might be identified as an opportunity for relatively high intensity radiation delivery.

Alternatively, a period of gated beam delivery may instead itself be regarded as being an opportunity to increase the intensity of the beam, when it is switched on, since each 'beam on' portion will naturally be followed by a 'beam off' portion of time, which will provide an opportunity for cooling down, or at least for no further heat to be generated. A selection may be made to increase the radiation delivery rate (i.e. to increase the intensity of radiation delivery) during at only some of the 'beam on' portions of an on/off gated beam delivery.

The present inventor has recognised that 'average heating' effects may be determined over relatively long periods of time, thus presenting one or more possible opportunities for relatively high intensity radiation delivery, within such periods of time. Nonetheless, any such opportunities—and, for example, the precise magnitude of the relatively high intensity radiation that should be delivered, and for how long and how often—should be balanced against a need to adhere to other operating constraints, including managing pulse heating effects. Factors such as ease of use for the device operator, and mitigating against possible operator confusion or error, may also have to be considered. In addition, it may be necessary to balance the potential increased complexity of treatment planning, and the increased time that such planning may involve, against the possible opportunity for improved efficiency of radiotherapy delivery.

There may also be clinical constraints to be balanced. In other words; from a clinical perspective, it may not always be appropriate to increase the intensity of radiation delivery to a particular target or patient, even if there are mechanical indicators suggesting that the radiotherapy device could safely do so.

Therefore the present inventor has recognised that an analysis may be carried out, to identify potential opportunities for the delivery of relatively high intensity radiation, by a radiotherapy delivery device, and to balance those opportunities against other constraints and operating and/or treatment factors. As discussed above, one motivating factor for increasing intensity of radiation delivery, to a target, may be to reduce the length of time for which a patient needs to be treated, per session (or 'fraction'), therefore reducing overall patient appointment time and thus enabling more appointments to be scheduled per day, thus enabling more efficient patient throughput. In other words; it may enable more patients to receive radiotherapy treatment, from a single radiotherapy device, per day (or per week, or per month, or per another suitable time period). Having a shorter radiotherapy session may also be attractive to patients.

Another possible motivating factor for increasing intensity of radiation delivery, to a target, may be to enable hypo-fractionation, of an individual's radiotherapy treatment plan. As the skilled reader will be aware, when a patient is prescribed radiotherapy treatment, usually a treatment plan is developed that prescribes the delivery of a predetermined amount of radiation, over a course of multiple radiotherapy sessions (or 'fractions'). The present inventor has recognised that, if opportunities for the delivery of relatively high intensity radiation are made use of, in an appropriate and balanced way, then the radiation dose prescribed within a treatment plan may be deliverable within fewer sessions, or fractions, than has previously been the case. This compacting of a treatment plan into fewer sessions may be referred to as 'hypo-fractionation'. Again, hypo-fractionation improves efficiency of radiotherapy delivery and allows higher patient throughput. It may also enable the beneficial clinical effects of radiotherapy to be experienced by an individual patient more quickly, and thus may contribute to more positive clinical results. Hypofractionation can improve the overall efficiency of a treatment plan because there are fewer sessions (or 'fractions'), and therefore fewer breaks, between sessions, therefore the plan and the clinician has to accommodate fewer inter-fraction motions of the patient's anatomy.

As mentioned above, the present inventor has recognised that cool-down periods will usually occur naturally, or inherently, within a patient's treatment plan, and also within a typical schedule, for a radiotherapy device. Therefore, the improved method disclosed herein can include identifying one or more cool-down periods, within a patient's treatment plan and/or within a schedule for a radiotherapy device, and selecting periods of time and/or portions of a treatment plan or schedule, that have an association, for example a temporal association, with a cool-down period (or periods). Those selected periods of time may be identified as being potentially suitable for applying radiation at a relatively high beam intensity. Those selected periods of time, and/or portions of a treatment plan or regime, which are potentially suitable for applying radiation at a relatively high beam intensity, may be referred herein to as 'boost' periods. This term is used for simplicity in this document and should not be regarded as being limiting.

A 'temporal association' between a cool-down period and a boost period may comprise any suitable temporal (i.e. time-related) link or connection. For example, a potential boost period may occur immediately before, or shortly before, a cool-down period. This would enable the heat-generating components of the radiotherapy device to generate heat at greater-than-average levels, during the boost period, and then to cool down soon afterwards, thereby avoiding or at least minimising the potential for heat damage. In some cases, a period of time may be identified as being a potential boost period if it would occur (e.g. start, or end, or occur in its entirety) within a predetermined time limit, before the occurrence of a subsequent cool down period.

There may be a relationship or rule (or a set, or plurality, of relationships or rules) determined between one or more characteristics of a boost period—such as the duration of the boost period and/or the extent to which radiation intensity would be increased during the boost period, and/or the amount of additional heat that the 'boost' would generate—and its associated cool-down period. For example, a rule may be applied wherein, the more additional heat that a boost period would create, the sooner a cool-down period would have to occur, after that boost period, in order for the boost to be permissible. For example, a rule may be applied wherein, the greater the extent to which radiation intensity would be increased during the boost period, the longer the required duration of the cool-down period would be. As the skilled reader will appreciate, these possible rules are examples only and should be regarded as being illustrative, not limiting. In practice, a set of rules or relationships governing whether and when a boost period can occur, and which characteristics it can have, may vary on a case-by-case basis, and will have a potentially large number of contributing factors. This is discussed further, later in the present application.

As discussed above, a cool-down period might be a scheduled stop or pause of radiation delivery, or it might be a time during which the radiation will only be delivered intermittently, and thus at a relatively low average intensity, over that cool-down period. If a radiotherapy device is configured to be able to deliver radiation at an intensity that is below its average intensity (e.g. below its 'default' intensity level), a cool-down period might comprise a period of time, or portion of a treatment schedule, during which radiation is scheduled to be delivered at that below-average level.

An association between a cool-down period and a boost period may comprise both of those periods being scheduled to occur within a common time window, for example within the same radiotherapy session, or fraction. An association between a cool-down period and a boost period may be established, in some circumstances, regardless of the chronology of, or of the temporal gap between, the two periods, within their common time window. It may be permissible for a boost period to occur if the total cool-down time available, within a common session or other time window, meets or exceeds a predetermined level or threshold, even if the cool-down period would occur over two or more sub-periods, within that time window. Similarly, it may be permissible to deliver a radiation boost over two or more sub-periods, within a session or other pre-determined time window.

In some cases, the improved methods disclosed herein may be provided in the form of an optimisation process, carried out in addition to conventional radiotherapy treatment planning methods. For example, an initial treatment plan may be determined for a patient, and partitioned into fractions (i.e. sessions), according to conventional methods. An optimisation may then be applied according to the presently-described methods. In such an optimisation, which may be an automated or a semi-automated process, control improvements may be made, to enable a radiotherapy device to deliver radiation at a higher-than-average intensity during one or more boost periods, which would be compensated for, in terms of heat generation, during one or more cool-down periods, as discussed above. Those cool-down periods may already be present, within the initial treatment plan or schedule, such that the net result of the optimisation may be to maintain the basic chronology of the steps to be carried out, according to the initial treatment plan, but to improve the plan's overall efficiency. This might comprise either reducing the total time for which radiation needs to be delivered, within the plan, and thus reducing the overall number of fractions and/or the length (in units of time) of one or more of the fractions.

Although the discussion above focuses on the identification of natural, or inherent, cool-down periods within a treatment plan or radiotherapy device schedule; it is also possible for cooling periods to be created, or at least to be deliberately scheduled in a certain manner, in order to provide or accommodate one or more opportunities for increasing the radiation intensity delivered at certain respective other times. Therefore, an optimisation process may comprise rescheduling one or more steps within a patient's treatment plan, or even adding one or more additional steps thereto, in order to enable a radiotherapy device to deliver radiation at a higher-than-average intensity during one or more 'boost' periods.

For example, within an individual fraction, or session, it may be possible to reorganise the chronology of certain steps—for example, changing the order in which different respective sub-targets are to be irradiated—if such a reorganisation would result in the creation of cool-down periods, which would permit the creation of associated 'boost' periods, during which the radiation could be delivered at a relatively high intensity. For example, in some cases it may be deemed beneficial to add in a period of cool-down, for which the radiation beam would be paused or stopped, in order to accommodate a boost period within the same fraction, or session. That additional cool-down period might occur, for example, at the end of the session, thus meaning that a longer-than-average break would have to be scheduled, for the radiotherapy device delivering the treatment, between that session and the next (i.e. subsequent) radiotherapy session. It may therefore be indicated in the patient's treatment plan that that particular fraction should be scheduled at the end of the day for the hospital clinic, or just before a natural break such as a lunch break.

Any rearrangement of pre-existing steps or addition of extra steps such as extra cool-down periods should only be carried out if its net effect would be positive, taking into account all relevant contributing factors. The contributing factors that are relevant may vary on a case-to-case basis. The determination of what constitutes a net positive (i.e. an overall beneficial or advantageous) effect may also vary on a case-to-case basis.

For example, it may be deemed to be net (i.e. overall) advantageous to add a cool-down period into a particular fraction of an individual patient's treatment plan, in order to enable one or more boost periods to also occur within that fraction and therefore to deliver more radiation to the patient, even if doing so extended the length (in units of time) of that particular fraction, if it enabled the patient's treatment plan to be hypo-fractionated. That is; it may be deemed overall most efficient to have fewer radiotherapy sessions, with one or more of those sessions (i.e. fractions) being longer than conventional sessions. However, for another patient, it may be deemed best to not to add any extra cool-down periods, and only to implement a boost period in a fraction of his or her treatment plan if a suitable pre-existing cool-down period would already be present, to offset the heating effects of such a boost period.

In some cases, it may be appropriate to apply the improved methods described herein to the schedule planning for a radiotherapy device (or for more than one radiotherapy device) in order to schedule particular radiotherapy appointments more efficiently and make use of boost periods for delivery of radiation at higher-than-average intensity. For example, a provider of radiotherapy may conduct an analysis of how many boost periods a radiotherapy device could safely deliver, and under what conditions, and may schedule appointments for different patients, and different radiotherapy needs, accordingly. For example, the provider may make use of pre-existing schedule breaks as cool-down periods, and identify corresponding potential boost periods accordingly. Patient appointments that include fractions comprising boost periods may then be scheduled in, to make use of as many opportunities for maximising efficiency of radiotherapy delivery by the radiotherapy device(s), whilst taking any other relevant scheduling considerations into account.

Although the examples above have referred to 'a' radiation beam, and its intensity, it is possible for the improved methods described herein to be applied to IMRT. As the skilled reader will know, IMRT (intensity modulated radiotherapy) applies a radiation beam that comprises a plurality of beamlets, wherein each beamlet can have an intensity that is controlled independently of the intensity of each of the respective others. Therefore different intensities of radiation can be applied across different parts of a target area, simultaneously. A barrier such as a multi-leaf collimator can be used to shape the beam in IMRT.

According to the improved methods described herein, a threshold for the maximum total permissible radiation intensity that can be applied by an entire IMRT beam may be increased, relative to conventional thresholds, and/or a threshold for the maximum permissible radiation intensity that can be applied by one IMRT beam let (or by a sub-group of IMRT beamlets, within a beam) may be increased, relative to conventional thresholds, during one or more 'boost periods'. As per the other examples above, this may enable more condensed, quicker radiotherapy sessions to be provided, and/or a treatment plan to be divided into fewer treatment fractions, if suitable cool-down periods are (or could be) present, in the schedule for a radiotherapy treatment fraction (and/or in the schedule for a radiotherapy device), to offset the thermal effects of the boost period(s).

Although the examples described above have focused on adding optimisation onto conventional treatment planning or scheduling methods; in some cases the improved methods described herein may be employed from the outset, in order to optimise a treatment plan or radiotherapy schedule during its creation. For example, a set of optimisation rules may be incorporated into an existing computer model for treatment planning. Therefore the optimisation would not be a separate step but would be an inherent part of the treatment planning or scheduling method. However, the same sort of rationale would apply, regardless of whether the optimisation is part of an initial plan creation process or is part of an additional step, for improving an existing plan.

Therefore, an improved radiotherapy treatment planning method (or an improved radiotherapy device schedule planning method) as disclosed herein may comprise identifying potential opportunities for providing radiation delivery at an intensity that is higher than the 'average' or 'default' intensity at which a radiotherapy device is currently set to operate, during one or more so-called 'boost periods', and identifying one or more 'cool-down periods', which would offset, or otherwise accommodate, the effects of the additional heat generation that the higher-than-average radiation generation during the boost periods would create. An improved treatment planning method as disclosed herein may further comprise incorporating any suitable identified boost periods (and any suitable corresponding cool-down periods) into a plan for delivering a course of radiotherapy treatment to a patient, in accordance with a prescription for treating one or more target areas in or on that patient's anatomy, with therapeutic radiation. The improved treatment planning method will usually comprise a 'cost-benefit' analysis, wherein the potential advantages of incorporating one or more boost periods into a radiotherapy plan are considered alongside other relevant factors such as, for example: safety; risk of heat-related damage to the radiotherapy device; both long and short term operational reliability of the radiotherapy device; financial cost; patient comfort; patient clinical goals and/or requirements; complexity of operating a radiotherapy device at different intensities, and/or of delivering a non-conventional treatment fraction, for the device operator; fairness of radiotherapy treatment provision to multiple different patients; planning time; complexity of planning; and so on.

As the skilled reader will appreciate, radiotherapy treatment planning is a complex procedure, with many contributary factors. Treatment planning is therefore usually carried out using (or with the assistance of) one or more computer-implemented models or algorithms or sets of algorithms. A physician who has responsibility for a patient's treatment will usually be required to approve a treatment plan, before it is put into practice, but may not be directly responsible for compiling the plan. As mentioned above, the improved methods described herein may be incorporated into the computer-implemented, or computer-assisted, treatment planning for radiotherapy, either as an additional optimisation step, once a plan has been created, and/or to optimise the creation of a treatment plan from the outset. This may involve optimisation considerations being incorporated into one or more models or other planning tools. Different models may be applied to different respective parts of a radiotherapy device—for example, one model may consider the heating effects on the waveguide and another may consider heating effects on the target. Alternatively, or additionally, one model may be used to consider instantaneous heating effects and another may be used to consider average heating effects.

If a model or models is/are used, it/they may be elf-learning, wherein new (or further or alternative) opportunities for introducing boost periods into a future treatment plan fraction may be identified through the observation of parameters that occur during delivery of radiotherapy to one or more patients. For example, a model for treatment planning might initially be trained to set a limit dictating the maximum permissible duration of a boost period, based on a first set of assumptions or predictions about the amount of additional heat that is created by the generation of radiation at higher-than-average intensity, per unit time, during a boost period. A treatment plan may be provided, based on that limit, and the radiotherapy prescribed in that treatment plan (or in one or more fractions of such a treatment plan) may be delivered to a patient. If, however, during that patient's treatment fraction(s) and/or during another patient's treatment fraction(s), the amount of additional heat generated per unit time in a boost period is observed or measured as being different to what was initially assumed or predicted, the model could be updated to amend the limit dictating the maximum permissible duration of a boost period, accordingly. In some cases, the updated model may be used to update future fractions of a patient's existing treatment plan. In other cases, the updated model may only be used for the creation of new (i.e. future) treatment plans. In some cases, there may be one or more thresholds or other rules, to determine whether an update to the self-learning model is significant enough to merit the amendment, or indeed the re-creation, of a treatment plan for one or more patients.

In some cases, a model or other treatment planning tool may be used, which includes a database or library of options for treatment delivery, wherein treatment planning comprises selecting from those options to compile a patient-appropriate treatment plan. In such cases, self-learning may comprise adding options to, and/or removing options from, that database or library, based on the experience gained through treatment delivery.

In some cases, a model or other set of rules may be created for each version (i.e. each 'model' or type), of a radiotherapy device, and applied to each individual device accordingly. In some cases, a scaling factor may be applied to the model or other set of rules, based on the inherent capabilities of an individual device. Some devices may be networked or otherwise communicatively coupled to a suitable processor, to feed measurements or other determinations back to the processor, for the purpose of self-learning. Model updates, based on self-learning or other factors, may be provided to multiple radiotherapy devices via appropriate software updates.

In conventional treatment planning methods, it is common for a proposed treatment plan to be based (inter alia) on a first set of images and to be checked, and possibly to be updated, based on a later (i.e. subsequently-obtained) set of images or later set of test results. The improved methods described herein may also accommodate such a step. The improved methods may therefore comprise updating a treatment plan, based on a set of images or tests, wherein the updating comprises optimising (or continuing to optimise) the treatment plan to include one or more boost periods and one or more cool-down periods. It will be appreciated that updating a treatment plan based on subsequently-obtained images or test results may necessitate the removal, or amendment, of a previously-scheduled boost period, from a treatment plan. Again, such a removal or amendment may be based on a cost-benefit (i.e. negative-versus-positive) analysis of the plan, taking into account a plurality of factors and applying one or more rules in order to determine the overall best available plan for the patient. In some cases, it may be possible not to optimise an initial treatment plan, and instead to only seek to optimise the treatment plan, to include boost periods and cool-down periods, at a late stage, for example a final stage, of planning, once all anticipated images and test results have been obtained.

The optimisation methods described herein could be undertaken in a Treatment Planning System and/or within a Delivery System for a radiotherapy device. In some cases, the optimisation could be shared between a Treatment Planning System and a Delivery System. Whichever system(s) or processor(s) is/are responsible for the optimisation should be provided with a model (or control map) of the relevant device/product, wherein the model would preferably be updated during the lifecycle of the product. The updates could encompass self-learning, as detailed above. The updates could also reflect mechanical developments such as component part changes and/or component wear and tear over time. The updates could enable enhanced optimisation, due to improvements as a result of self-learning or other developments.

The improved methods may be further understood in relation to the following examples, which should be understood to be illustrative and not to be limiting.

According to an example, improved control is provided of the operation of a radiotherapy device for delivery of a radiotherapy treatment beam to a target volume that is subjected to periodic motion, within a patient's anatomy. For example, the target volume could be subjected to periodic motion caused by respiration. The motion could be of the target volume itself and/or of tissue surrounding or otherwise near the target volume. In such an example, it is known to monitor the movement of the target volume and to only apply radiation thereto when the target volume (and/or the relevant other tissue) is in a particular position. For example, the radiotherapy device may only apply radiation during an exhale, not during an inhale. Such treatment is typically controlled by providing a gated delivery regime, wherein the beam is effectively intermittently switched on and off, in a manner that aligns with the periodic motion of the target volume (or of tissue surrounding or otherwise near the target volume).

In conventional techniques, the calculation of the heating effects of a gated radiation delivery regime typically treats the entire delivery time period, including the portions of time for which the beam is switched off, as being 'beam on' time. The present inventor has recognised, however, that the actual 'beam on' time is shorter than that, and that taking into account the gated nature of the radiation delivery enables a much more accurate determination of the heat generated by the beam generation apparatus, during a gated beam delivery, to be made. The present inventor has therefore recognised that the 'beam on' portions of a gated radiation beam delivery regime may be suitable as 'boost periods', during which radiation would be delivered at a higher-than-average intensity (i.e. at a higher rate of radiation supplied per unit time than is the current average or default for a radiotherapy device), with the 'beam off' portions of the regime serving as corresponding cool-down periods. As a result, more radiation can be delivered to the target volume, when the beam is switched on and being applied to the target volume. This can result in either the time required for delivery of a prescribed dose of radiation to be reduced and/or the amount of radiation being delivered in a single session or fraction of a treatment plan being increased. The treatment plan may therefore be delivered over fewer fractions, hence reducing the number of radiotherapy sessions that the patient has to attend, and creating availability within the schedule for the radiotherapy device.

It will be appreciated that not all anatomical motion is periodic motion. The improved methods described herein may be applied to target volumes that are subjected to other types of motion, and which thus are suitable for intermittent application of radiation thereto.

One particular example of tissue that is subjected to motion is the heart. In cases which require ablation of heart tissue—i.e. radiation to be applied to heart tissue—both respiratory motion and blood circulatory motion must be taken into account. This leaves a relatively narrow (i.e. short), intermittent, window (or, in practice, plurality of windows) of opportunity available for irradiating heart tissue. The present inventor has therefore recognised that it may be advantageous to supply radiation to heart tissue at a relatively high intensity, when possible, in order to apply condensed doses of radiation over the relatively short, intermittent available time windows. A treatment plan may therefore treat one or more of the 'beam on' portions of heart ablation as a 'boost period', with one or more 'beam off' portions serving as corresponding a 'cool-down period'. As per the other examples above, a treatment planning or optimisation process would only implement such 'boost' and 'cool-down' periods if and when an analysis deemed it appropriate, and the precise length, frequency, number and radiation intensity of any such periods would be determined, by taking a number of factors into account including, for example, safety, based on the thermal properties of the radiotherapy device, time-efficiency, patient wellbeing and so on.

The improved methods described herein may be applicable to static radiotherapy—in which the patient and radiotherapy device both remain stationary, when a radiotherapy beam is being applied—and to dynamic radiotherapy, in which the radiation source is continually moved, relative to patient support surface, during application of the radiotherapy beam. An example of dynamic radiotherapy is VMAT (volumetric modulated arc therapy), which is a type of IMRT radiotherapy, as mentioned earlier in the present disclosure.

It is known for dynamic radiation techniques such as VMAT to be planned and/or controlled using an optimiser, which can comprise any suitably-programmed computer or other processor. Within a typical VMAT optimisation process, the optimiser would consider the dynamics of movements and dose rate, and would determine how the radiation beam(s) should be reshaped and/or changed, in terms of intensity, as the radiation source moves around the patient's body. The improved methods described herein may be incorporated into such as optimisation process. Thus, an optimiser would have the ability to provide one or more boost periods, to optimise dose rate further, in circumstances in which conventional thermal thresholds have previously been a limiting factor, if there is a known 'cooling' period of lower dose rate identified, in connection with (e.g. occurring shortly after) the boost period(s). The improved methods may also enable the order in which different segments, within a VMAT treatment arc, are delivered to be changed, in order to accommodate boost periods for certain segments and to provide appropriate corresponding cool down periods.

An optimiser could therefore consider the potential for identifying and prescribing boost periods as another degree of freedom in its optimisation. In multi-arc optimisations, an optimiser could change the sequence of its control points to ensure the treatment time is fully optimised, wherein it chooses to optimise dose rate, through the provision of higher intensity radiation during one or more boost periods. One example of a suitable optimiser for such a processor is an iterative, converge-type optimiser, however this should not be regarded as being a limiting example. According to an example, it may be possible to harvest a plurality of treatment plans and their corresponding optimiser results and to feed them into a deep learning algorithm, which would provide an iterative optimiser with a 'warm start', thus shortening the time taken by it to optimise (i.e. to plan the optimisation of) the delivery of future treatment plans.

Figure 3:
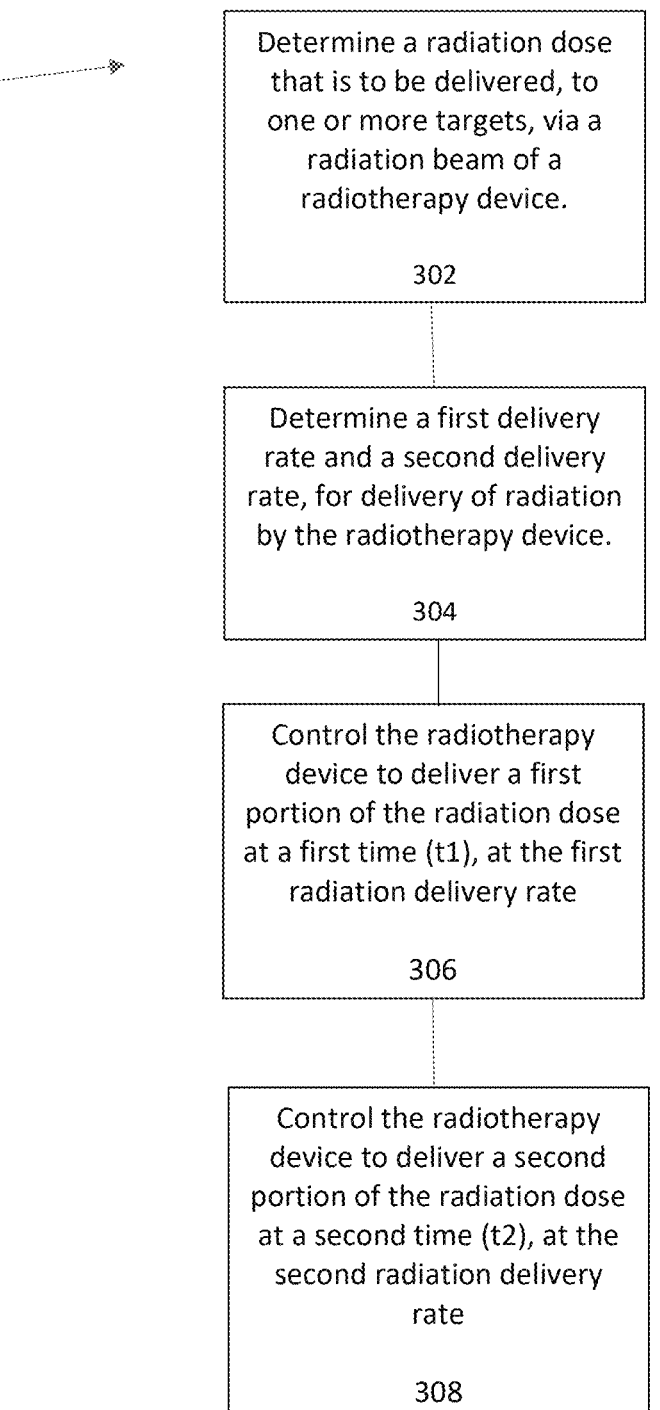
FIG. 3 is an overview of an improved method of controlling a radiotherapy device.

By way of summary; FIG. 3 shows an improved method of controlling a radiotherapy device, as detailed hereabove. This summary is an overview only—further details can be found in the preceding description.

The method 300 optionally comprises, at step 302, determining a radiation dose that is to be delivered, to one or more targets, via a radiation beam of a radiotherapy device. This may comprise calculating a radiation dose. This may comprise simply obtaining the radiation dose from, for example, a patient-specific treatment plan.

The radiotherapy device comprises a beam generation apparatus that is selectively configurable to output radiation via a radiotherapy treatment beam at either of a first radiation delivery rate or a second radiation delivery rate. The method therefore further comprises, at step 304, determining a first delivery rate and a second delivery rate, for delivery of radiation, by the radiotherapy device. This step may be inherent, as the first and second delivery rates may be pre-configured for the radiotherapy device, at least for an individual patient and/or for a particular target type. This step may, in some cases, involve calculating or otherwise determining either the first delivery rate and/or the second delivery rate.

The method further comprises, at step 306, controlling the radiotherapy device to deliver a first portion of the radiation dose at a first time (t1), at the first radiation delivery rate.

The method further comprises, at step 308, controlling the radiotherapy device to deliver a second portion of the radiation dose at a second time (t2), at the second radiation delivery rate.

The first portion plus the second portion may be equal to the entire radiation dose. The total heat generated by delivery of the first portion at the first delivery rate at the first time (t1) and delivery of the second portion at the second radiation delivery rate at the second time (t2) may be controlled so as not to exceed one or more limits, such as a safety limit and/or a heat threshold.

In an implementation, method 300 is performed while ensuring that at least one criterion associated with an operational parameter of the radiotherapy device is met. For example, while ensuring that a constraint associated with the operational parameters is not exceeded. In particular, the first and second times may be identified, e.g. scheduled, in order to ensure the operational parameter meets a criterion throughout treatment.

In an implementation, the operational parameter may be the heat generated at a component of the radiotherapy device, and the at least one criterion may be that a predefined heat threshold should not be exceeded during treatment/during implementation of the control scheme. In this implementation, the radiotherapy device is controlled at steps 306 and 308 such that a pre-determined heat threshold for the radiotherapy device is not exceeded. As described elsewhere herein, this can be achieved by adjusting a ratio between the size of a first portion of the radiation dose delivered via the first delivery rate, and the size of a second portion of the radiation dose delivered via the second delivery rate.
Asynchronous Pulse Control As described above, and as well-known to the skilled reader, a radiation beam is delivered as a series of pulses, which are delivered at a Pulse Repetition Frequency (PRF). The PRF of a radiotherapy device tends to be quick, for example it may be set at several hundreds of pulses per second. In addition, and as per certain examples above, there are circumstances in which the delivery of a radiation beam, to a target area, must be gated—i.e. intermittently switched on and off (or, intermittently blocked and unblocked). This can be, for example, to accommodate anatomical motion. According to conventional techniques, when a radiotherapy device, or system, delivers a beam of megavolt (MV) radiation energy, in a gated delivery scheme, the PRF is not altered, nor is the triggering of the radiation pulses synchronised with the gating scheme (i.e. with the switching on and off of the radiation beam). This being the case, when a 'beam on' portion of a gated radiation delivery scheme begins, conventionally a radiotherapy system simply has to wait for a pulse to occur.

The present inventor has therefore recognised that a particular application of the improved methods, devices, and/or systems described herein may enable the delivery of radiation in a gated delivery scheme to be optimised—for example, to deliver more radiation within a 'beam on' window—by improving the timing of pulses within a 'beam on' portion of a gated delivery scheme. The present inventor has recognised that the relative timing of pulse delivery and gating for a radiation beam may be controlled, for example using a control scheme. The control scheme may comprise instructions which cause the radiotherapy device to operate, e.g. deliver radiation, according to any of the methods described herein. The control scheme might be described as a delivery scheme herein. The control scheme contains instructions which cause treatment to be delivered in a particular way, for example according to a treatment plan. The control scheme may comprise instructions which, when executed by the radiotherapy device, cause the device to deliver radiation at the delivery rates and at times determined according to methods disclosed herein.

In particular, the inventors have recognised that a 'beam on' portion of a gated radiation delivery scheme may be configured as a 'boost period', in which a higher-than-average intensity of radiation is delivered per unit time, by controlling the number of pulses of radiation that are emitted and thus applied to the patient, during the 'beam on' portion (or 'beam on' time window). As with the other examples above, an analysis may be conducted to determine the suitability of one or more 'beam on' portions for being a boost period, and to identify one or more corresponding cool-down periods, during which a lower intensity of radiation per unit time (or no radiation) would be delivered, in order to offset the thermal effects of the additional radiation generation, during the boost period(s).

If one or more 'beam on' portions of a gated (or otherwise intermittent) radiation delivery schemed are identified as being suitable for high intensity radiation delivery, a controller comprised within, or communicatively connected to, the radiotherapy device can control the pulsing of the radiation, so that more pulses of radiation would occur within a 'beam on' time window, than would be expected during a conventional gated radiation delivery scheme. For example, the controller may control an internal clock that triggers the radiation pulses, to provide a radiation pulse that is asynchronous with the other pulses, within a pre-set PRF. For example, the timing may be controlled to ensure that an 'asynchronous' radiation pulse is delivered immediately, at the beginning of a 'beam on' time window. Dependent on the relative length of the 'beam on' time window, and the gap between pulses, this may enable an additional pulse to be delivered, within the 'beam on' time window. Therefore, additional radiation may be delivered, per 'beam on' window. Although this may seem to be a relatively small change, the skilled reader will appreciate that its effects can be significant, in certain circumstances. For example, in the case of heart tissue ablation, which is mentioned above, the available window of time for 'beam on' tends to be very short. Providing an asynchronous pulse of radiation, at the very beginning of a 'beam on' time window for heart ablation may therefore enable, for example, two radiation pulses to be delivered within that time window, instead of just one. Therefore the radiation intensity can be increased significantly, as compared with conventional techniques.

In another example, the controller may control an internal clock that triggers the radiation pulses to provide several radiation pulses at once (i.e. one immediately following the other), with a period of exposure such as a 'beam on' window of a gated radiation delivery scheme, rather than pulsing intermittently, as per the conventional PRF, during that window. Again, an analysis may be conducted, to ensure the thermal effects of such an intense delivery of radiation pulses could be accommodated by one or more corresponding cool-down periods. However the present inventor has determined that, at least in some circumstances—for example, when there are relatively long delays between relatively short 'beam on' windows of time, for example during heart ablation or irradiation of other motion-sensitive tissue—it will be possible to apply intense radiation in short bursts of multiple pulses, in this manner, whilst still adhering to safety requirements and not causing intolerable heat damage to a radiotherapy device. Thus the improved methods, devices, and/or systems described herein can be employed to achieve a more deterministic, more optimised, less random approach to radiotherapy delivery, in a gated or otherwise intermittent delivery scheme.

The improved methods described herein allow the optimisation of radiation delivery control, by optimisation of the thermal characteristics of a radiotherapy device. The improved methods can be implemented as a software-based solution, applied to pre-existing hardware. They do not require the addition of, for example, an additional RF source, nor do they require any other physical changes to be made to an existing radiotherapy device. Moreover, improvements or modifications to the methods described herein may be delivered via appropriate software updates. For example, the set of rules or algorithms that govern the presence of one or more boost periods, and any limits or boundaries for radiation delivery within those boost periods, may change as part of a self-learning process, or based on externally-derived learnings, or as a result of the age of the radiotherapy device, including anticipated wear and tear, and so on.

The improved methods described herein enable the delivery of radiation, during therapeutic radiotherapy, to be controlled and to be optimised. The improved methods make use of pre-existing thermal characteristics of a radiotherapy device—for example, its ability to withstand relatively high amounts of heat generation, for limited periods of time, and/or if offset by corresponding cooler periods—and use them to apply a more intelligent, nuanced control than is currently achievable, using conventional radiotherapy techniques. The improved methods do not rely on assumptions of continuous steady-state operation of a radiotherapy device, during a given day or even during a scheduled radiotherapy appointment. Instead, they recognise that, in practice, a radiotherapy device may have relatively long periods of inactivity, or at least of low-intensity radiation output, interspersed amongst its periods of activity. The improved methods therefore use this recognition to determine whether 'boost periods' may be identified, during which radiation can be output at a relatively high intensity rate—for example, at an intensity that exceeds a conventional average or 'default' intensity for a particular radiotherapy device—and what the nature of those boost periods might be. For example, the nature may include the duration and/or frequency and/or timing of one or more boost periods, and the permissible level of radiation intensity during one or more boost periods.

The improved methods apply intelligent analysis to determine whether, when and how a higher-than-average intensity of radiation might be output. They enable different factors to be considered in different respective circumstances, as part of a cost-benefit analysis, to determine whether, and under what conditions, having a boost period during delivery of radiotherapy treatment may have an overall positive (i.e. beneficial) effect. They also enable different rules to be applied, dependent on the particular details of a case, to determine what constitutes a net (i.e. overall) beneficial effect. For example, in some circumstances, it may be appropriate to prioritise time efficiency, per fraction of a radiotherapy treatment regime, and therefore to use boost periods to reduce the overall length (in units of time) of each fraction. In other circumstances, it may be preferable to extend the duration of a particular fraction, for example due to the presence of an extra cool-down period, to offset one or more boost periods, if it enables a reduction in the number of fractions into which the treatment plan must be divided (i.e. if it enables hypofractionation.)

It may be appropriate, when carrying out the improved methods described herein, to balance what is theoretically possible against what is practical, in a real radiotherapy planning and/or delivery environment. For example, one or more rules or thresholds may be put in place, to ensure that a optimisation process does not output a suggested treatment plan that is excessively complex to deliver, in practice, for a radiotherapy technician. Patient comfort and wellbeing should also be considered, for example when determining how long a radiotherapy session could be and/or how intense a delivered dose of radiation should be, at any time.

The improved methods enable significant increased efficiency of control and operation of a radiotherapy device, but at relatively low financial cost and without requiring the addition of undue complexity or any significant lengthening of existing treatment planning and control processes. For example, the improved methods can lead to shorter radiotherapy application times, thus shortening patient appointments and enabling increased patient throughput, for a radiotherapy provider. Shorter appointments also reduce the risk of complexities arising from unexpected, or unpredictable anatomical motion, during radiotherapy delivery. The scope for hypofractionation, as a result of the improved methods described herein, can also enable the reduction of inter-fraction motion management complexities (including clinical, technical and user related steps), by reducing the number of fractions, and therefore the number of breaks between fractions, of a radiotherapy treatment delivery plan.

The order of execution or performance of the operations as described herein is not essential, unless otherwise specified. That is, the operations may be performed in any order, unless otherwise specified, and embodiments of may include additional or fewer operations than those disclosed herein. For example, executing or performing a particular operation before, contemporaneously with, or after another operation is contemplated.

The words "comprising," "having," "containing," and "including," and other similar forms are intended to be open ended, such that an item or items following any one of these words is not meant to be an exhaustive listing of the item or items, nor meant to be limited to only the listed item or items. And the singular forms "a," "an," and "the" are intended to include plural references, unless the context clearly dictates otherwise.

Figure 4:
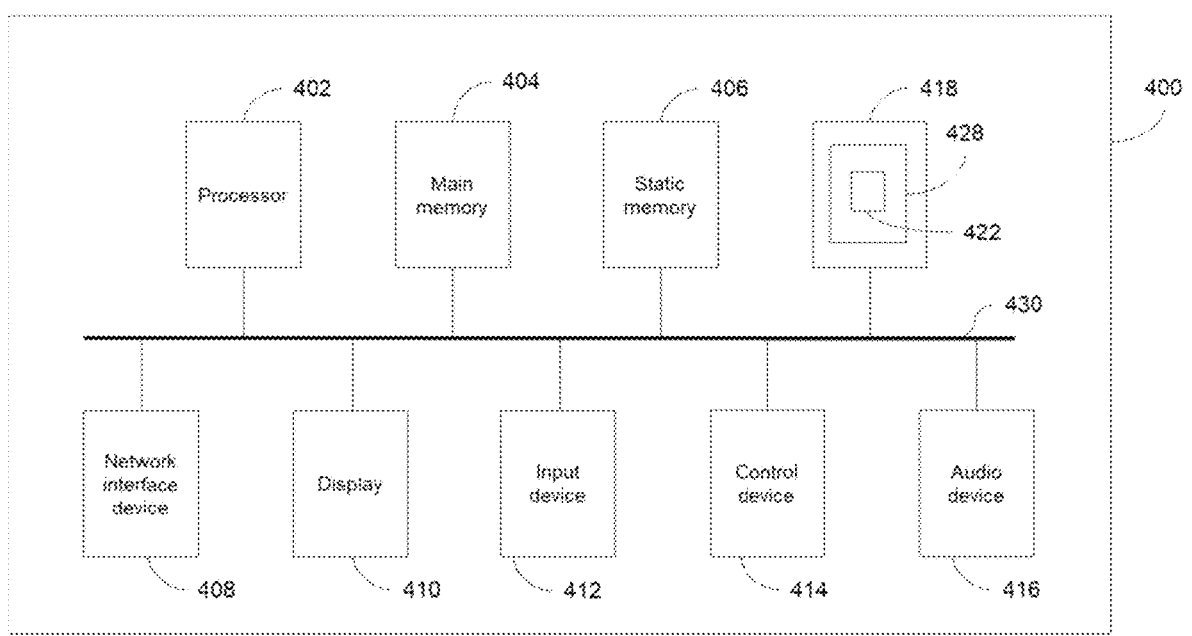
FIG. 4 shows a computer that may perform the methods of the present disclosure.

FIG. 4 illustrates a block diagram of one implementation of a computing device 400 within which a set of instructions, for causing the computing device to perform any one or more of the methodologies discussed herein, may be executed. In alternative implementations, the computing device may be connected (e.g., networked) to other machines in a Local Area Network (LAN), an intranet, an extranet, or the Internet. The computing device may operate in the capacity of a server or a client machine in a client-server network environment, or as a peer machine in a peer-to-peer (or distributed) network environment. The computing device may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single computing device is illustrated, the term "computing device" shall also be taken to include any collection of machines (e.g., computers) that individually or jointly execute a set (or multiple sets) of instructions to perform any one or more of the methodologies discussed herein.

The example computing device 400 includes a processing device 402, a main memory 404 (e.g., read-only memory (ROM), flash memory, dynamic random access memory (DRAM) such as synchronous DRAM (SDRAM) or Rambus DRAM (RDRAM), etc.), a static memory 406 (e.g., flash memory, static random access memory (SRAM), etc.), and a secondary memory (e.g., a data storage device 418), which communicate with each other via a bus 430.

Processing device 402 represents one or more general-purpose processors such as a microprocessor, central processing unit, or the like. More particularly, the processing device 402 may be a complex instruction set computing (CISC) microprocessor, reduced instruction set computing (RISC) microprocessor, very long instruction word (VLIW) microprocessor, processor implementing other instruction sets, or processors implementing a combination of instruction sets. Processing device 402 may also be one or more special-purpose processing devices such as an application specific integrated circuit (ASIC), a field programmable gate array (FPGA), a digital signal processor (DSP), network processor, or the like. Processing device 402 is configured to execute the processing logic (instructions 422) for performing the operations and steps discussed herein.

The computing device 400 may further include a network interface device 408. The computing device 400 also may include a video display unit 410 (e.g., a liquid crystal display (LCD) or a cathode ray tube (CRT)), an alphanumeric input device 412 (e.g., a keyboard or touchscreen), a cursor control device 414 (e.g., a mouse or touchscreen), and an audio device 416 (e.g., a speaker).

The data storage device 418 may include one or more machine-readable storage media (or more specifically one or more non-transitory computer-readable storage media) 428 on which is stored one or more sets of instructions 422 embodying any one or more of the methodologies or functions described herein. The instructions 422 may also reside, completely or at least partially, within the main memory 404 and/or within the processing device 402 during execution thereof by the computer system 400, the main memory 404 and the processing device 402 also constituting computer-readable storage media.

The various methods described above may be implemented by a computer program. The computer program may include computer code arranged to instruct a computer to perform the functions of one or more of the various methods described above. The computer program and/or the code for performing such methods may be provided to an apparatus, such as a computer, on one or more computer readable media or, more generally, a computer program product. The computer readable media may be transitory or non-transitory. The one or more computer readable media could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations.

A hardware component may be or include a special-purpose processor, such as a field programmable gate array (FPGA) or an ASIC. A hardware component may also include programmable logic or circuitry that is temporarily configured by software to perform certain operations.

Accordingly, the phrase "hardware component" should be understood to encompass a tangible entity that may be physically constructed, permanently configured (e.g., hard-wired), or temporarily configured (e.g., programmed) to operate in a certain manner or to perform certain operations described herein.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

Unless specifically stated otherwise, as apparent from the following discussion, it is appreciated that throughout the description, discussions utilizing terms such as "receiving", "determining", "comparing", "enabling", "maintaining," "identifying," or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Disclosed herein is a method of controlling operation of a radiotherapy device for delivery of a radiotherapy treatment beam, the radiotherapy device comprising a beam generation apparatus that is selectively configurable to output radiation via a radiotherapy treatment beam at either of a first radiation delivery rate or a second radiation delivery rate, wherein the second radiation delivery rate is higher than the first radiation delivery rate. The method comprises determining a radiation dose that is to be delivered, to one or more targets and controlling the radiotherapy device to deliver a first portion of the radiation dose at a first time (t1), at the first radiation delivery rate and to deliver a second portion of the radiation dose a second time (t2), at the second radiation delivery rate.

Also disclosed herein is a radiotherapy device for delivery of a radiotherapy treatment beam, the radiotherapy device comprising a beam generation apparatus that is selectively configurable to output radiation via a radiotherapy treatment beam at either of a first radiation delivery rate or a second radiation delivery rate, wherein the second radiation delivery rate is higher than the first radiation delivery rate. The radiotherapy device is configured to deliver a radiation dose to a target, wherein a first portion of the radiation dose is delivered, at the first radiation delivery rate, at a first time (t1) and a second portion of the radiation dose is delivered, at the second radiation delivery rate, at a second time (t2).

Also disclosed herein is a method of determining a control scheme for operating a radiotherapy device to deliver a radiotherapy treatment beam, wherein the radiotherapy device comprises a beam generation apparatus that is selectively configurable to output radiation via a radiotherapy treatment beam at either of a first radiation delivery rate or a second radiation delivery rate, wherein the second radiation delivery rate is higher than the first radiation delivery rate. The method comprises determining a radiation dose that is to be delivered, to one or more targets, by the radiotherapy device, identifying a first time (t1) at which a first portion of the radiation dose is to be delivered, at the first radiation delivery rate; and identifying a second time (t2) at which a second portion of the radiation dose is to be delivered, at the second radiation delivery rate. Optionally, the method may further comprise determining the control scheme based on the determined first and second time. The control scheme may thus comprise instructions which, when executed by a controller of a radiotherapy device, cause the device to deliver a first portion of the radiation dose at the first delivery rate and at the first identified time (t1); and deliver the second portion of the radiation dose at the second delivery rate and at the second identified time (t2).

It is to be understood that the above description is intended to be illustrative, and not restrictive. Many other implementations will be apparent to those of skill in the art upon reading and understanding the above description. Although the present disclosure has been described with reference to specific example implementations, it will be recognized that the disclosure is not limited to the implementations described, but can be practiced with modification and alteration within the spirit and scope of the appended claims. Accordingly, the specification and drawings are to be regarded in an illustrative sense rather than a restrictive sense. The scope of the disclosure should, therefore, be determined with reference to the appended claims, along with the full scope of equivalents to which such claims are entitled.

The following numbered clauses are disclosed herein.

1. A method of controlling operation of a radiotherapy device for delivery of a radiation dose via a radiotherapy treatment beam to one or more targets;

the radiotherapy device comprising a beam generation apparatus that is selectively configurable to output radiation via a radiotherapy treatment beam at either of a first radiation delivery rate or a second radiation delivery rate, wherein the second radiation delivery rate is higher than the first radiation delivery rate;

the method comprising controlling the radiotherapy device to:

deliver a first portion of the radiation dose at a first time (t1), at the first radiation delivery rate; and deliver a second portion of the radiation dose a second time (t2), at the second radiation delivery rate.

2. The method of clause 1 wherein the first radiation delivery rate comprises a default delivery rate for the beam generation apparatus.

3. The method of clause 1 wherein the first radiation delivery rate comprises a default maximum delivery rate threshold for the beam generation apparatus.

4. The method of any preceding clause further comprising controlling the radiotherapy device to undergo a cool-down period at a third time (t3).

5. The method of clause 4 wherein the third time (t3) and the second time (t2) occur within a pre-determined common time window.

6. The method of any preceding clause wherein the target comprises one or more target regions on or within a patient's body.

7. The method of any preceding clause wherein each of the first time (t1) and the second time (t2) comprises one or any combination of: one or more instantaneous times; one or more pulse durations and one or more continuous time periods.

8. The method of any preceding clause wherein there is a pre-determined heat threshold for the radiotherapy device and wherein the method comprises controlling operation of the radiotherapy device to ensure that a ratio between the size of the first portion of the radiation dose and the size of the second portion of the radiation dose is in accordance with that heat threshold.

9. The method of any preceding clause wherein the target is subject to anatomical motion.

10. The method of clause 9, when dependent on clause 4, wherein the third time (t3) is a time at which the target, or a part of the target, will exhibit a pre-determined motion characteristic.

11. The method of any preceding clause further comprising controlling the radiotherapy treatment beam to be intermittently applied to a target, during at least part of the second time (t2).

12. The method of any preceding clause wherein the radiotherapy treatment beam comprises a plurality of radiation pulses, emitted at a pulse repetition frequency (PRF), the method further comprising controlling the emission of one or more radiation pulses to coincide with an occurrence of the second time (t2).

13. The method of any preceding clause wherein the method is a computer-implemented method.

14. The method of any preceding clause, further comprising receiving and/or determining the radiation dose that is to be delivered.

15. A radiotherapy device for delivery of a radiotherapy treatment beam;

the radiotherapy device comprising a beam generation apparatus that is selectively configurable to output radiation via a radiotherapy treatment beam at either of a first radiation delivery rate or a second radiation delivery rate, wherein the second radiation delivery rate is higher than the first radiation delivery rate;

the radiotherapy device being configured to deliver a radiation dose to a target; wherein a first portion of the radiation dose is delivered, at the first radiation delivery rate, at a first time (t1); and a second portion of the radiation dose is delivered, at the second radiation delivery rate, at a second time (t2).

16. A method of determining a control scheme for operating a radiotherapy device to deliver a radiation dose via a radiotherapy treatment beam to one or more targets;
   the radiotherapy device comprising a beam generation apparatus that is selectively configurable to output radiation via a radiotherapy treatment beam at either of a first radiation delivery rate or a second radiation delivery rate, wherein the second radiation delivery rate is higher than the first radiation delivery rate;
   the method comprising:
   identifying a first time (t1) at which a first portion of the radiation dose is to be delivered, at the first radiation delivery rate; and
   identifying a second time (t2) at which a second portion of the radiation dose is to be delivered, at the second radiation delivery rate.
17. The method of clause 15 wherein there is a pre-determined heat threshold for the beam generation apparatus, the method comprising increasing the size of the second portion, relative to the first portion, to decrease the total delivery time for the radiation dose, without exceeding the pre-determined heat threshold for the beam generation apparatus.
18. The method of clause 16 or clause 17, wherein the control scheme comprises instructions which cause the radiotherapy device to operate according to any of clauses 1 to 14.
19. A method of controlling operation of a radiotherapy device for delivery of a radiotherapy treatment beam;
   the beam generation apparatus being configured to output the radiotherapy treatment beam as a plurality of radiation pulses, at a pulse repetition frequency (PRF);
   the radiotherapy device being selectively configurable to apply the radiotherapy treatment beam intermittently to a target, during a pre-determined time window, such that the pre-determined window comprises at least a first period of time during which the beam is applied to the target and a second period of time, during which the beam is not applied to the target;
   the method comprising controlling the emission of one or more radiation pulses to coincide with an occurrence of the first period of time.
20. The method of clause 19 comprising controlling the emission of a radiation pulse to occur substantially at the beginning of the first period of time.
21. The method of clause 19 or clause 20 comprising increasing the pulse repetition frequency (PRF), during the first period of time.
22. A computer program comprising instructions which, when executed by a computer, causes the computer to perform a method according to any of clauses 1 to 14 or 16 to 21.
23. A computer readable medium having stored thereon a computer program according to clause 22.
24. A data carrier signal carrying the computer program of clause 22.
25. A data processing apparatus for a radiotherapy system, the data processing apparatus comprising a processor configured to perform the method of any of clauses 1 to 14 or 16 to 21.

The invention claimed is:
1. A computer-implemented method of determining a control scheme for operating a radiotherapy device for a delivery of a radiation dose via a radiotherapy treatment beam to a target, the radiotherapy device comprising:
   a beam generation apparatus that is configured to output radiation via a radiotherapy treatment beam, wherein an operation of the radiotherapy device includes a use of at least one operational parameter, wherein the at least one operational parameter is heat generated at a component of the radiotherapy device;
   the computer-implemented method comprising determining the control scheme by:
   identifying a first time (t1) at which at least a first portion of the radiation dose is to be delivered at a first radiation delivery rate; and
   identifying a second time (t2) for the radiotherapy device to undergo a cool-down period, wherein during the cool-down period, a second radiation delivery rate is less than the first radiation delivery rate, and wherein the control scheme is determined such that at least one criterion associated with the at least one operational parameter is met, wherein the at least one criterion is that a predefined heat threshold should not be exceeded.
2. The computer-implemented method of claim 1, wherein the second radiation delivery rate during the cool-down period is zero.
3. The computer-implemented method of claim 1, wherein the second radiation delivery rate during the cool-down period comprises a threshold of a default maximum delivery rate for the beam generation apparatus.
4. The computer-implemented method of claim 1, wherein the first time (t1) and the second time (t2) occur within a pre-determined common time window.
5. The computer-implemented method of claim 1, wherein the second time (t2) is a time at which the target, or a part of the target, will exhibit a pre-determined motion characteristic, during which the delivery of the radiation dose to the target is inhibited.
6. The computer-implemented method of claim 1, wherein the target is subject to an anatomical motion, and determining the control scheme further comprises:
   receiving information indicative of a movement of the target with respect to a treatment volume through which the radiotherapy treatment beam will pass; and:
   identifying the first time (t1) such that the at least a first portion of the radiation dose is delivered while the target is at least partly located within the treatment volume; and/or
   identifying the second time (t2) such that the cool-down period occurs while the target is at least partly located outside the treatment volume.
7. The computer-implemented method of claim 1, wherein the target comprises one or more target regions on or within a body of a patient.
8. The computer-implemented method of any preceding claim 1, wherein each of the first time (t1) and the second time (t2) comprises at least one of: one or more instantaneous times, one or more pulse durations, or one or more continuous time periods.
9. The computer-implemented method of claim 1, wherein the at least one criterion is that the at least one operational parameter of the radiotherapy device must be kept below a threshold throughout an implementation of the control scheme.
10. The computer-implemented method of claim 1, wherein the first radiation delivery rate is determined, and/or the first time (t1) is identified, based on the at least one operational parameter of the radiotherapy device.

11. The computer-implemented method of claim 1, wherein the at least one operational parameter of the radiotherapy device further comprises any of a voltage, a current, power, or heat, and/or wherein the at least one operational parameter of the radiotherapy device is associated with at least one component of the radiotherapy device, and wherein the at least one component of the radiotherapy device comprises any of a magnetron, an RF window, an RF circulator, a cooling system, or the beam generation apparatus.

12. The computer-implemented method of claim 1, wherein the radiotherapy device has a pre-determined heat threshold, and wherein the computer-implemented method further comprises:

determining the control scheme such that an amount of heat generated during the first time (t1) and an amount of heat generated during the cool-down period does not exceed the pre-determined heat threshold, wherein a second portion of the radiation dose is delivered during the cool-down period, and wherein determining the control scheme such that the amount of heat generated during the first time (t1) and the amount of heat generated during the cool-down period does not exceed the pre-determined heat threshold comprises ensuring that a ratio between a size of the first portion of the radiation dose and a size of the second portion of the radiation dose is in accordance with the pre-determined heat threshold.

13. The computer-implemented method of claim 1, wherein the control scheme comprises instructions which, when implemented, cause the radiotherapy device to apply the radiotherapy treatment beam intermittently to the target, during at least part of the first time (t1).

14. The computer-implemented method of claim 1, wherein the radiotherapy treatment beam comprises:

a plurality of radiation pulses, emitted at a pulse repetition frequency (PRF), wherein the control scheme comprises instructions which, when implemented, cause the radiotherapy device to emit one or more radiation pulses, which coincide with an occurrence of the first time (t1).

15. The computer-implemented method of claim 1, wherein the control scheme comprises instructions which, when implemented, cause the radiotherapy device to:

deliver the at least a first portion of the radiation dose at the first time (t1) and at the first radiation delivery rate; and

deliver a second portion of the radiation dose at the second time (t2) and at the second radiation delivery rate, wherein the beam generation apparatus has a pre-determined heat threshold, and the computer-implemented method further comprising:

increasing a size of the second portion of the radiation dose, relative to the first portion of the radiation dose, to decrease a total delivery time for the radiation dose, without exceeding the pre-determined heat threshold for the beam generation apparatus.

16. The computer-implemented method of claim 1, wherein determining the control scheme further comprises:

scheduling a plurality of first times at which radiation is to be delivered at the first radiation delivery rate, and a plurality of second times at which the radiotherapy device is to undergo a cool-down period, and wherein the control scheme is determined such that the at least one criterion is met throughout an implementation of the control scheme.

17. A radiotherapy device for a delivery of a radiotherapy treatment beam, the radiotherapy device comprising:

a beam generation apparatus that is configured to output radiation via a radiotherapy treatment beam, wherein an operation of the radiotherapy device includes use of at least one operational parameter, wherein the at least one operational parameter is heat generated at a component of the radiotherapy device, wherein the component is one of a magnetron, an RF window, an RF circulator, a cooling system or the beam generation apparatus, and wherein the radiotherapy device is configured to deliver a radiation dose to a target; and a processor configured to determine a control scheme according to at least one criterion associated with the at least one operational parameter, wherein the at least one criterion is that a predefined heat threshold should not be exceeded, and wherein the determined control scheme comprises instructions which, when implemented by the processor of the radiotherapy device, cause the radiotherapy device to:

deliver at least a first portion of the radiation dose at a first radiation delivery rate at a first time (t1); and undergo a cool-down period, wherein during the cool-down period a second radiation delivery rate is less than the first radiation delivery rate.

* * * * *